(12) United States Patent
Akella et al.

(10) Patent No.: US 11,348,033 B2
(45) Date of Patent: May 31, 2022

(54) COMPUTATIONAL ANALYSIS OF OBSERVATIONS FOR DETERMINATION OF FEEDBACK

(71) Applicant: SRI International, Menlo Park, CA (US)

(72) Inventors: Prasad Narasimha Akella, Palo Alto, CA (US); Bhaskar Ramamurthy, Los Altos, CA (US); Manish Kothari, San Carlos, CA (US); John Peter Marcotullio, Morgan Hill, CA (US)

(73) Assignee: SRI International, Menlo Park, CA (US)

( * ) Notice: Subject to any disclaimer, the term of this patent is extended or adjusted under 35 U.S.C. 154(b) by 711 days.

(21) Appl. No.: 16/318,667

(22) PCT Filed: Jul. 21, 2017

(86) PCT No.: PCT/US2017/043325
§ 371 (c)(1),
(2) Date: Jan. 17, 2019

(87) PCT Pub. No.: WO2018/017973
PCT Pub. Date: Jan. 25, 2018

(65) Prior Publication Data
US 2019/0266514 A1 Aug. 29, 2019

Related U.S. Application Data

(60) Provisional application No. 62/365,508, filed on Jul. 22, 2016.

(51) Int. Cl.
*G06N 20/00* (2019.01)
*G06Q 10/06* (2012.01)
(Continued)

(52) U.S. Cl.
CPC ......... *G06N 20/00* (2019.01); *G05B 23/0254* (2013.01); *G06F 15/16* (2013.01);
(Continued)

(58) Field of Classification Search
CPC ....... H04L 41/16; H04L 41/069; H04L 43/16; G06N 20/00; G06F 15/16
See application file for complete search history.

(56) References Cited

U.S. PATENT DOCUMENTS 10,320,813 B1 * 6/2019 Ahmed ............... H04L 63/1441
2005/0222813 A1 10/2005 Bjornson
(Continued)

OTHER PUBLICATIONS

Ferguson, D., "Therbligs: The Keys to Simplifying Work," The Gilbreth Network, 2000, 10 pp. (Applicant points out, in accordance with MPEP 609.04(a), that the year of publication, 2000, is sufficiently earlier than the effective U.S. filing date, so that the particular month of publication is not in issue.).

(Continued)

*Primary Examiner* — El Hadji M Sall
(74) *Attorney, Agent, or Firm* — Shumaker & Seiffert, P.A.

(57) ABSTRACT

A system comprises one or more observation stations. Each observation station of the one or more observation stations comprises a corresponding set of one or more sensors. Additionally, the system comprises one or more physical machines that implement a computation engine configured to receive first observation data from the one or more observation stations. The computation engine may use the first observation data to train a machine learning system. The computation engine may subsequently use the trained machine learning system to provide feedback regarding an additional instance of the observation subject. The computation engine outputs the feedback.

20 Claims, 10 Drawing Sheets

(51) Int. Cl.
*G06F 15/16* (2006.01)
*G05B 23/02* (2006.01)
*G16H 40/20* (2018.01)
*G16H 20/40* (2018.01)
*G16H 40/40* (2018.01)

(52) U.S. Cl.
CPC ......... *G06Q 10/06* (2013.01); *G06Q 10/0633* (2013.01); *G16H 20/40* (2018.01); *G16H 40/20* (2018.01); *G16H 40/40* (2018.01); *Y02P 90/02* (2015.11)

(56) References Cited

U.S. PATENT DOCUMENTS

| | | |
|---|---|---|
| 2008/0263491 A1 | 10/2008 | Foltz et al. |
| 2009/0089701 A1 | 4/2009 | Baier et al. |
| 2010/0211670 A1 | 8/2010 | Caldwell |
| 2012/0029678 A1 | 2/2012 | McGreevy et al. |
| 2013/0103764 A1* | 4/2013 | Verkasalo ............. G06Q 30/02 709/204 |
| 2013/0282609 A1 | 10/2013 | Au et al. |
| 2014/0047107 A1 | 2/2014 | Maturana et al. |
| 2014/0234814 A1* | 8/2014 | Krosky ............. A63B 69/0028 434/236 |
| 2014/0351642 A1 | 11/2014 | Bates et al. |
| 2015/0254555 A1* | 9/2015 | Williams, Jr. ....... G06N 3/0454 706/14 |
| 2015/0364021 A1 | 12/2015 | Ur |
| 2016/0202074 A1* | 7/2016 | Woodard ............... G01C 21/34 701/465 |
| 2017/0019315 A1* | 1/2017 | Tapia .................... G06N 20/00 |
| 2018/0011953 A1* | 1/2018 | Micks ................... G06N 20/00 |

OTHER PUBLICATIONS

Perkins, J.S., "Frank B. Gilbreth's Research: The Quest of the One Best Way," The Quest, The Newsletter of the Gilbreth Network, vol. 1, No. 2, Summer 1997, 7 pp. (Applicant points out, in accordance with MPEP 609.04(a), that the year of publication, 1997, is sufficiently earlier than the effective U.S. filing date, so that the particular month of publication is not in issue.).

Sirkin et al., "The Robotics Revolution: The Next Great Leap in Manufacturing," The Boston Consulting Group, Sep. 2015, 28 pp. (Uploaded in 2 parts).

Yeung et al., "End-to-End Learning of Action Detection from Frame Glimpses in Videos," Proceedings of the IEEE Conference on Computer Vision and pattern Recognition (CVPR), Feb. 2016, 10 pp.

International Preliminary Report on Patentability from International Application No. PCT/US2017/043325, dated Jan. 31, 2019, 11 pp.

International Search Report and Written Opinion of International Application No. PCT/US2017/043325, dated Sep. 29, 2017, 12 pp.

* cited by examiner

COMPUTATIONAL ANALYSIS OF OBSERVATIONS FOR DETERMINATION OF FEEDBACK

This application claims the benefit of U.S. Provisional Application 62/365,508, filed Jul. 22, 2016, the entire contents of which are incorporated by reference.

BACKGROUND

Although automation in manufacturing has been widely adopted and is pervasive, a large portion of manufacturing is still manual in nature. According to a report published by the Boston Consulting Group (BCG) in 2016, 90% of manufacturing today is manual. See e.g., "The Robotics Revolution: The next great leap in manufacturing," The Boston Consulting Group, 2016, https://www.bcgperspectives.com/content/articles/lean-manufacturing-innovation-robotics-revolution-next-great-leap-manufacturing/. Even in an environment where automation is utilized, there is still a need to utilize human operators. Many issues arise due to the existence of this man-machine interface as humans introduce variance into these processes due to their very human nature. Thus, to reduce the variability, there is a need to conduct frequent inspections to ensure that the product and process meet the required performance metrics. The results of the inspections are analyzed and are utilized to improve metrics like quality, productivity, throughput, warranty and recall rates. Today, many techniques are utilized to conduct these inspections including having dedicated inspection stations, doubling up on human operators so that one operator can observe the other, cameras that feed their output to a central observation station, etc. While this need can be readily understood in a manufacturing scenario, the situation and needs are similar in diverse fields from safely conducting surgeries in hospitals to making burgers in fast food restaurants.

SUMMARY

Given the variability introduced by human operators, there may be a need to observe humans and machines in these man-machine systems in order to understand how tasks are being performed, the performance being measured using appropriate metrics. Additionally, there may be a further need is to then find ways to improve a process being used to deliver a product. Typically, even in state-of-the-art manufacturing floors, these two functions of observation and analysis are performed by disparate systems. An even further need may be to create a knowledge base of various manufacturing practices and to provide tools so that this knowledge base can be queried and the results can be applied to a multitude of purposes such as but not limited to improving part design, suggesting floor plans, improving recall rates, and limiting the financial impact of recalls.

To address the issues above, a feedback generation system is described that has multiple functions including, but not limited to, being able to observe and analyze the observed data and other data. In some examples, the feedback generation system includes one or more observation stations that generate observation data. Thus, observations may be accomplished by installing one or more observation stations that generate observation data. Each observation station may include one or more sensors such as, but not limited to, cameras, infrared sensors, motion trackers, position sensors, thermal sensors and audio microphones. An observation station may be stationary, mobile, worn on the head of the operator, or of some other configuration. The observation data generated by an observation station may include sensor data from the one or more sensors included in the observation station.

Furthermore, the feedback generation system comprises a computation engine. The computation engine may use the observation data from the observation stations as a training set to train a machine learning system. The observation subject may be a process performed at one or more factories, a step of the process, a task of the step of the process, an action of the task, a part used or made as part of the process, or other type of subject. Thus, in some examples, when the machine learning system is sufficiently trained, the computation engine may be able to use the trained machine learning system to identify whether an instance of the observation subject is represented in newly received sets of observation data from the same or different observation stations. As part of training the machine learning system, the observation data can be processed by one or several sub-engines, such as but not limited to, an analysis engine and a process-discovery engine. The output of these engines can be fed back locally to improve the machine learning system.

The feedback generation system can also have various architecture configurations. In some configurations, the entire architecture of the feedback generation system is placed locally. In other configurations, a distributed architecture is utilized. In a distributed architecture, some processing is done locally but some other processing is done remotely, e.g., in the cloud. The results can be made available locally or can be made available globally. In either case, depending on the system settings such as privacy settings, the results can contribute and add to a knowledge base.

A product manufactured in a factory can generally pass through three phases—pre-factory, in-factory, and post-factory. A factory, in the context of this disclosure, can include but may not be limited to manufacturing plants, operating theatres (e.g., for surgery), stores, restaurants, offices, or other locations where humans and/or machines perform routinized processes, tasks, or activities. Pre-factory activities include product design. In-factory activities include process design and personnel selection and quality measurement. Post-factory factory activities include warranty and recall. The feedback generation system described in this disclosure may address all three phases and may provide to feedback to optimize each of the phases, individually and as a whole. In contrast, companies that provide data and insights about factory processes, typically address one or perhaps two of these phases. For example, companies that provide benchmarking data typically rely on surveys that are done in the post-factory phase.

In some examples, the work output of manufacturing facilities as measured by metrics such as efficiency, throughput, recall rates or other parameters, can be improved, driven by a holistic understanding of the various factors influencing the manufacture of a product. In some examples, results of analysis can be applied locally and globally. For instance, an insurance company, not involved in the manufacture of a specific product providing warranty against defective labor, can set the rates of the product from one company based on the knowledge of product quality of the same type of product from other companies. In some situations, worker satisfaction may improve if, for example, the observation station is able to observe the human operators for parameters such as but not limited to posture and eye-strain and suggest improvements to the ergonomics of their individual environments."

In one example, this disclosure describes a system comprising: one or more observation stations, each observation station of the one or more observation stations comprising a corresponding set of one or more sensors; and one or more physical machines that implement a computation engine configured to: receive first observation data from the one or more observation stations, the first observation data comprising sensor data collected from observing instances of an observation subject, the observation subject being in a group consisting of: a process performed at one or more factories, a step of the process, a task of the step of the process, an action of the task, and a part used or made as part of the process; train, based at least in part on the first observation data, a machine learning system; receive, after the machine learning system has been trained, second observation data from the one or more observation stations, the second observation data comprising sensor data collected from observing an additional instance of the observation subject; use the trained machine learning system to determine feedback based at least in part on the second observation data, the feedback comprising at least one of: an indication of how to improve the additional instance of the observation subject and an indication that the additional instance of the observation subject differs from a reference model; and output the feedback.

In another example, this disclosure describes a method comprising: receiving, by one or more physical machines that implement a computation engine, first observation data comprising sensor data collected from observing instances of an observation subject, the observation subject being in a group consisting of: a process performed at one or more factories, a step of the process, a task of the step of the process, an action of the task, and a part used or made as part of the process; training, by the computation engine, based at least in part on the first observation data, a machine learning system; receiving, by the computation engine, after the machine learning system has been trained, second observation data from the one or more observation stations, the second observation data comprising sensor data collected from observing an additional instance of the observation subject; using, by the computation engine, the trained machine learning system to determine feedback based at least in part on the second observation data, the feedback comprising at least one of: an indication of how to improve the additional instance of the observation subject and an indication that the additional instance of the observation subject differs from a reference model; and outputting, by the computation engine, the feedback.

In another example, this disclosure describes a computing system comprising one or more physical machines that implement a computation engine configured to: receive first data, the first data comprising at least one of: first observation data from one or more observation stations or first input data, the first observation data comprising sensor data collected from observing instances of an observation subject, the observation subject being in a group consisting of: a process performed at one or more factories, a step of the process, a task of the step of the process, an action of the task, and a part used or made as part of the process, the first input data comprising one or more of: a first process chart, first video data, first audio data, a first consumer satisfaction report, first recall data, and first insurance data; train, based at least in part on the first data, a machine learning system; receive, after the machine learning system has been trained, second data from the one or more observation stations, the second data comprising at least one of: second observation data or second input data, the second observation data comprising sensor data collected from observing an additional instance of the observation subject, the second input data comprising one or more of: a second process chart, second video data, second audio data, a second consumer satisfaction report, second recall data, and second insurance data; use the trained machine learning system to determine feedback based at least in part on the second data, the feedback comprising at least one of: an indication of how to improve the additional instance of the observation subject and an indication that the additional instance of the observation subject differs from a reference model; and output the feedback.

The details of one or more aspects of the disclosure are set forth in the accompanying drawings and the description below. Other features, objects, and advantages of the techniques described in this disclosure will be apparent from the description, drawings, and claims.

DETAILED DESCRIPTION

Figure 1A:
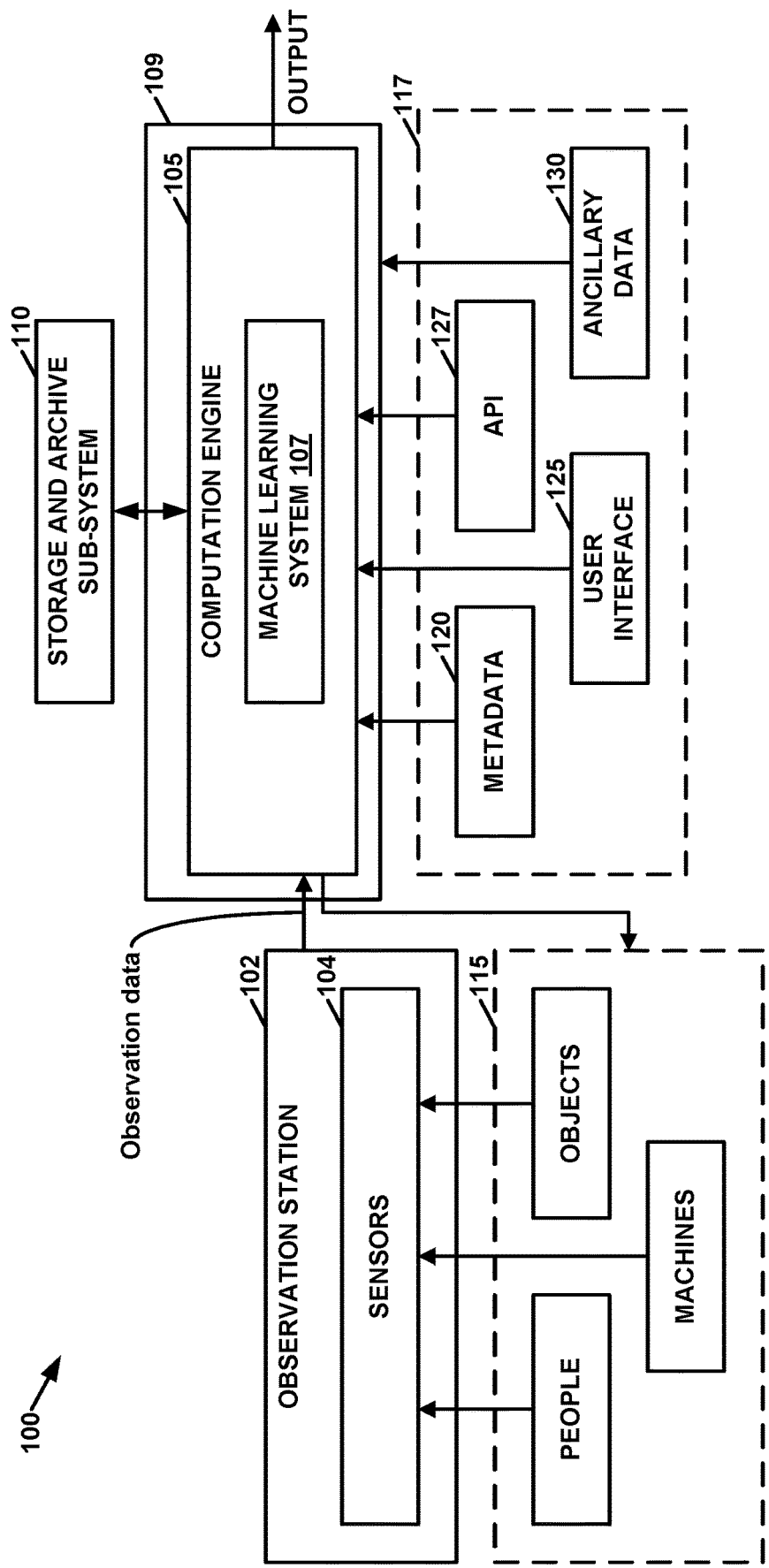
FIG. 1A illustrates an example manager system, in accordance with one or more aspects of this disclosure.

FIG. 1A illustrates an example manager system 100 (e.g., a manager station), in accordance with one or more aspects of this disclosure. In this configuration, manager system 100 comprises at least an observation station 102, a computation engine 105, and a storage and archival sub-system 110. Other configurations of manager system 100 are explained below.

Observation station 102 accepts input from one or more sensors 104. For instance, observation station 102 may comprise one or more sensors 104. Examples of sensors 104 include, but are not necessarily limited to, visible light cameras, infrared cameras, motion sensors, accelerometers, thermometers, virtual reality systems, augmented reality systems and Radio Frequency Identification (RFID) tags. This disclosure may also refer to observation stations as observation systems.

In some examples, the components of observation station 102, including sensors 104, are contained within one physical structure. In some examples, the components of observation station 102 are mounted individually on an existing work-cell infrastructure. Further, in examples where the components of observation station 102 are contained in one physical structure, observation station 102 may be mounted on wheels so that observation station 102 can be rolled easily from one location to another. In some examples, the wheels of observation station 102 can be motorized or can be manually operated.

In some examples, observation station 102 may be docked with an environment that observation station 102 is observing. In one example configuration, components of observation station 102 may also be mounted on an operator (e.g., on the forehead). This configuration may be advantageous in minimizing, if not avoiding, occlusions as the operator can naturally or deliberately reposition his or her head to obtain a better view of the task. Observation station 102 may, in some examples, be combined with augmented reality systems, which may have the benefit that more information and metadata such as contextual information may be provided to the operator. Observation station 102 may also provide its own lighting so that reliance on ambient lighting may be reduced or removed.

Observation station 102 may be set up to observe one or multiple parameters 115. For example, observation station 102 may be set up to observe parameters 115 such as, but not limited to, people, machines, objects, and the environment. In some examples, observation station 102 is positioned at a workstation. In this disclosure, a workstation is a location at which one or more tasks are performed in a step of a process performed at a factory. For example, a workstation may be a location where a human worker works. In another example, a workstation may be a location where a robot performs one or more tasks. In some examples, a workstation may be referred to as a work-cell.

In one example of how observation station 102 may be set up, consider a board manufacturing assembly line. In this example, observation station 102 may comprise one or multiple cameras placed so that one camera may be focused on the hand motions of an operator working in a workstation in the board manufacturing assembly line and another camera may be focused on a specific part that was being mounted on a board.

Observation station 102 feeds data (i.e., observation data) from one or multiple of sensors 104 to computation engine 105. The observation data provided by observation station 102 may comprise sensor data collected from observation station 102 observing instances of an observation subject. For instance, the observation subject may be a process performed at one or more factories, a step of the process, a task of the step of the process, an action of the task, and a part used or made as part of the process. Parameters 115 may include people, machines, and objects involved in the process, step, task, or action. In examples where the observation subject is a part used or made as part of the process, an object in parameters 115 may be the observation subject.

Computation engine 105 may be implemented using one or more physical computing devices 109. For example, computation engine 105 may be implemented using a cluster of one or more server devices, server blades, personal computers, mobile computing devices, and/or other types of computing devices. For clarity, computing devices 109 are omitted from the remaining figures. However, it should be understood that in the context of other figures, computation engines are implemented on one or more physical computing devices. In some examples, observation station 102 has screens or monitors that computation engine 105 can use to communicate messages, warnings or courses of action to the operators at the workstation.

In addition to receiving observation data from observation station 102, computation engine 105 may accept inputs 117 in various forms. For example, computation engine 105 may receive such input from an operator as metadata 120, through a user interface 125, through an application programming interface (API) 127, or as ancillary data 130. Metadata 120 may comprise data about objects, machines, people, or other parameters observed by observation station 102. User interface 125 may comprises a graphical user interface, a command line interface, or another type of user interface that receives indications of user input from a user. API 127 may comprise an interface through which a software application can interact with computation engine 105. For instance, a software application may use API 127 to provide information to computation engine 105. Ancillary data 130 may comprise data from business systems including, but not limited to, an inventory management system or personnel files.

Computation engine 105 may also interface to a storage and archival sub-system 110. Storage and archival sub-system 110 may be implemented using one or more computing devices, such as Network Attached Storage (NAS) devices, Storage Area Network (SAN) devices, server devices, or other types of computing devices. In some examples, the same set of one or more computing devices may implement both computation engine 105 and storage and archival sub-system 110. Storage and archival sub-system 110 may store data various types of data. For example, storage and archival sub-system 110 may store observation data received from observation stations, such as observation station 102, inputs 117, outputs of computation engine 105, reference data, and other types of data.

Computation engine 105 may provide several outputs. For example, computation engine 105 may provide a real-time, dynamic feedback on how to optimize an activity or other observation subject being observed. The process of determining the output is termed dynamic optimization in this disclosure. Dynamic optimization may be real-time, quasi real-time, or non-real time. Optimization may include, but may not be limited to, optimizing the duration of a task being performed, assignment of tasks, the order in which the tasks are performed or where the tasks are being performed and by whom.

Computation engine 105 may perform this dynamic optimization in various ways. In the example of FIG. 1, computation engine 105 uses observation data to train a machine learning system 107. For example, computation engine 105 may train machine learning system 107 to identify whether additional observation data represents an instance of a task being performed at a workstation. In some examples, training machine learning system 107 may comprise use of machine learning techniques to determine reference data against which additional observation data can be compared. Although machine learning system 107 may be trained and used in examples of other figures of this disclosure, machine learning system 107 is omitted for reasons of clarity.

After sufficient training has occurred, computation engine 105 may use machine learning system 107 to determine feedback. For example, if observation station 102 subsequently observes a certain process containing several tasks, computation engine 105 may analyze the observation data from observation station 102 to determine the amounts of time each task takes. Computation engine 105 may also determine the dependency of each task to previous tasks or to conditions in the environment. Once this is all observed and the dependencies are known, much like a program management tool that optimizes a project, observation station 102 can also optimize or suggest a new order of tasks. In another example, observation station 102 may observe the same task, but may be in a different process in a different factory. In this example, if a certain way of doing a task is more efficient (as evidenced by task analysis above) then computation engine 105 may propagate this knowledge.

Other outputs may include, but are not necessarily limited to, training videos or procedures, suggestions for parts redesign, etc. For example, computation engine 105 may identify a reference process based on observation data that comprises videos of the process or of each task within the process. Computation engine 105 may subsequently receive observation data representing a worker at a particular workstation. Computation engine 105 may use the trained machine learning system to determine that the worker is performing the process, but there are differences between how the worker is performing the process and the identified reference process. Accordingly, computation engine 105 may play back, at the particular workstation, the previously-received video best representative of the identified reference process. In this way, an operator at the workstation may see how to perform the identified reference process. This disclosure provides details of various outputs below.

Figure 1B:
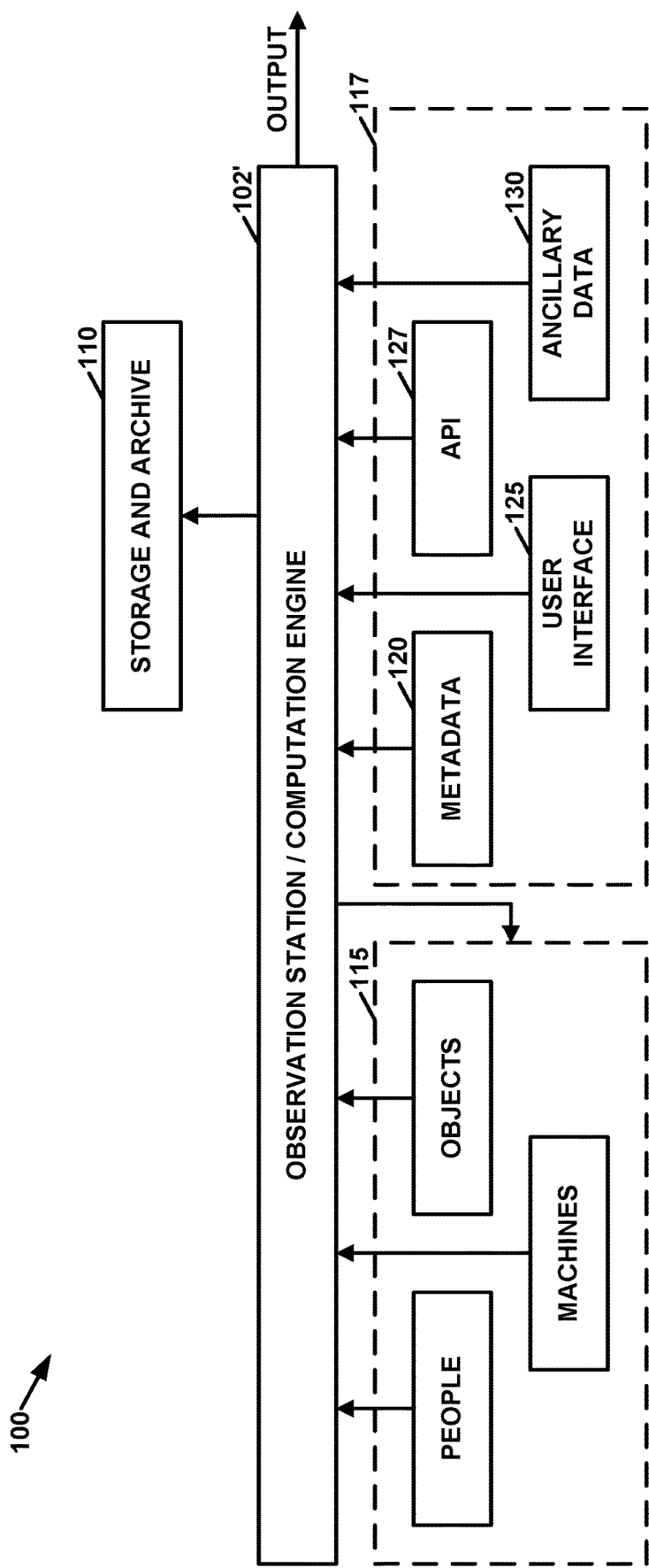
FIG. 1B is a block diagram illustrating an example manager system in which an observation station and a computation engine are located in one physical entity, in accordance with one or more aspects of this disclosure.

As noted above, several configurations of manager system 100 are possible. FIG. 1A shows an example where observation station 102, computation engine 105 and storage and archival sub-system 110 are located in separate physical entities. In FIG. 1B, box 102' illustrates that observation station 102 and computation engine 105 are located in one physical entity. In other words, FIG. 1B is a block diagram illustrating an example manager system in which an observation station and a computation engine are located in one physical entity, in accordance with one or more aspects of this disclosure. Other distributions of sub-engines across physical entities are also possible, as described later in the context of FIG. 4 and FIG. 5.

To provide better understanding of examples in this disclosure, the following terms are defined below:
- A "process" consists of a series of steps in order to achieve a particular goal;
- A "step" consists of a series of tasks in order to achieve one part of the goal (or the sub-goal);
- A "task" consists of a series of actions in order to complete one part of a step;
- An "action" consists of a series of atomic actions in order to complete one part of a task. An example of an action may be "pick up a chip".
- An "atomic action" is the smallest unit of activity.

Based on this, the phrase "a process" indicates the underlying components such as a step, a task, an action and an atomic action. Hence for example when a "process" is being observed, then all the underlying step or steps, task or tasks and action or actions, atomic action or actions are also being observed.

Figure 2:
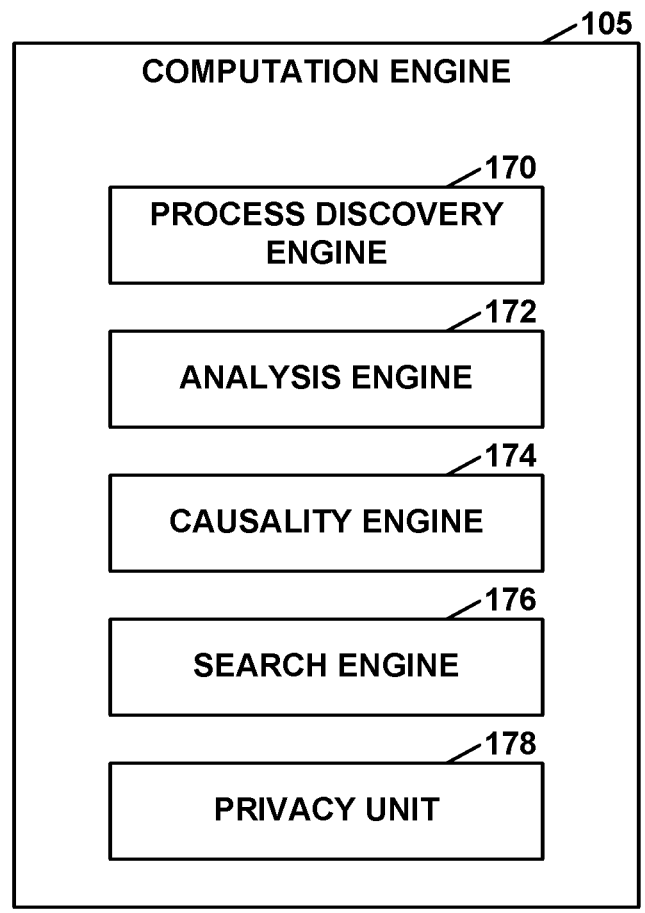
FIG. 2 is a block diagram illustrating example sub-engines of computation engine, in accordance with one or more aspects of this disclosure.

FIG. 2 is a block diagram illustrating example sub-engines of computation engine, in accordance with one or more aspects of this disclosure. As shown in the example of FIG. 2, computation engine 105 may comprise several sub-engines such as, but not necessarily limited to, a process discovery engine 170, an analysis engine 172, a causality engine 174, a search engine 176, and a privacy unit 178. For instance, in some examples, all of the functions local to observation station 102 to the functions are distributed. In some examples, the sub-engines (e.g., process discovery engine 170, analysis engine 172, causality engine 174, search engine 176, and privacy unit 178) may be distributed in various ways across the physical systems or machines. A description of these sub-engines is provided further below.

As noted above, computation engine 105 may include an analysis engine 172. In general, analysis engine 172 observes a task and produces information about the task. For example, analysis engine 172 may determine how long a task takes to complete, a success rate of the task, an initial position and final position of a part involved in a task, and so on. The function of analysis engine 172 is described with an example. In this example, an operator at a workstation is lifting a part, such as an integrated circuit (IC), from a specific bin amongst a row of bins and inserting the part into a socket at a specific location with a specific orientation on a printed circuit board (PCB). A video camera is installed to observe this process. Manager system 100 may make multiple observations of this process and from these observations, analysis engine 172 may manually or automatically build a statistical model. In other words, analysis engine 172 may train, based on the observation data, a machine learning system. Thus, in the above example, observation station 102 observes a parameter that describes the spatio-temporal characteristic of the part. Mathematically, this parameter can be described, for example, as a seven-dimensional space-time vector:

$$\vec{P} = \begin{bmatrix} t \\ x \\ y \\ z \\ \alpha \\ \beta \\ \gamma \end{bmatrix}$$

where vector $\vec{P}$ describes the space-time vector that describes the spatio-temporal location of the part. In this vector, t corresponds to time; x, y, and z correspond to Cartesian coordinates; $\alpha$ corresponds to pitch; $\beta$ corresponds to yaw, and $\gamma$ corresponds to roll. Through observations, analysis engine 172 of computation engine 105 can find the initial and final values of $\vec{P}$ (i.e. $\vec{P}_i$ and $\vec{P}_f$). In addition, analysis engine 172 may calculate the statistics associated with each variable in the seven-dimension vector such as, but not necessarily limited to, an expected value, a standard deviation and maximum values. In other examples, additional variables including but not limited to temperature and sound are recorded and are part of the vector $\vec{P}$.

Thus, in this example, if the observed initial or final vector falls outside a predefined or calculated set of threshold values for each of the seven variables in the vector, then analysis engine 172 may flag an anomaly or error. In some examples, the output of computation engine 105 may include an indication of the anomaly or error. Furthermore, flagging an anomaly or error can, in some examples, trigger a set of actions aimed at correcting or rectifying the situation (e.g., instantly or at a later time). Thus, in this example, after analysis engine 172 has determined the vector (i.e., after the machine learning system has been trained), analysis engine 172 may receive additional observation data that comprises sensor data collected from observing another instance of observation subject (i.e., a task of the operator lifting a part from a specific bin amongst a row of bins and inserting the part into a socket at a specific location with a specific orientation on a PCB). Furthermore, in this example, analysis engine 172 may use the vector to determine feedback based on the additional observation data (i.e., determine observed vector falls outside set of threshold values). In this example, computation engine 105 may output the feedback (i.e., flag the anomaly or error).

Analysis engine 172 may have other additional features. In one additional feature, analysis engine 172 is capable of change detection. That is, analysis engine 172 can analyze a scene and determine if the scene is different from a reference scene. Examples related to how a reference scene can be generated are described further below. However, if a difference is detected between a current scene and a reference scene, analysis engine 172 may flag a deviation (which could be an error). In the example of the IC being picked up, analysis engine 172 may flag an error if a different IC was picked up or if the IC was placed in an inverted position. In this example, analysis engine 172 was not supplied with any additional data other than what observation station 102 can observe. However, in some examples, analysis engine 172 may be supplied with additional data such as, but not limited to, metadata about the IC, optimal solder temperature can be included for more advanced analysis. Metadata about the IC can inform analysis engine 172 about specific details about the IC that may be useful in the identification and/or placement of the IC. In addition, information about the placement methodology may be useful in estimating the quality and reliability of the product containing that IC.

A reference scene may be defined as a scene that best describes what is to be expected in a scene at a specific location. The reference scene may be generated in multiple ways. In one example, a human operator selects the reference scene based on knowledge about the actions at a specific location. In another example, analysis engine 172 may automatically select the reference scene from a set of scenes obtained through multiple observations. The automatic selection may be guided by a statistical technique. In other words, assuming that a scene is a collection of one or multiple objects each object having an appropriate location with some statistical distribution of the location, a reference scene can be constructed by specifying the desired objects and their desired locations. Each of the desired locations can be specified in terms of a mean expected value and a threshold or boundary. Thus, a reference scene can be specified as a scene where a desired set of objects are in specific positions within some boundary values. The boundary values can be different for each object. Not all objects in the scene may need to be included in the desired set of objects.

In some examples, analysis engine 172 is capable of object detection, action recognition and change detection. Object detection may be implemented using different techniques. In one technique, a statistical technique is utilized. Consider an object, O. From the many observations of O, analysis engine 172 builds an understanding of dimensions of O, along with an estimate of the associated errors and confidence levels, based on descriptive statistics. Thus, O(l), the length of the object is expressed as l±e, where l is the length and e the acceptable error in its measurement. In another instance, object detection can be done by drawing upon an existing database of knowledge. This database of knowledge may be built by training manager system 100 by providing manager system 100 with camera data, Computer Assisted Design (CAD) data or other data and associating the data with an object. In this example, an existing database of such information may also be imported and may be used. In another variation, object detection can be achieved by having domain experts identify and tag the different objects in previously recorded scenes. Objects may include but may not be limited to ICs, discrete parts like resistors, capacitors, power transformers, and circuit boards. Objects may also include human hands, gloves, fingers, tweezers, soldering irons, etc. The amount of knowledge may be built over time and may be made available to other instances of manager systems through cloud services.

The action recognition capability also may rely on existing knowledge. In this case, manager system 100 may rely on a vocabulary of atomic actions where each atomic action forms the smallest individual or a group of actions that is necessary to form a bigger action. The concept of atomic actions has been previously described by Frank Gilbreth and Lillian Gilbreth. See e.g., David Ferguson, "Therbligs: The keys to simplifying work," The Quest, Newsletter of the Gilbreth Network, 2000, http://gilbrethnetwork.tripod.com/therbligs.html; James S. Perkins, "Frank B. Gilbreth's Research: The Quest of the One Big Way," The Quest, Newsletter of the Gilbreth Network, Vol. 1, No. 2, 1997; Frank B. Gilbreth, Ernestine Gilbreth Cary, "Cheaper By the Dozen," Harper Collins ISBN 978-0-06-076313-8, http://gilbrethnetwork.tripod.com/qv1n2.html. In this work, a vocabulary of 18 elemental motions or "Therbligs" was defined in order to break down tasks to their most basic elements. For example, in the Therblig notation a "Retrieve Object" action, may be described as (i) search (ii) find, (iii) select (iv) grasp. These "atomic" actions collectively describe the "Retrieve Object" action. Thus, an action at a scene may be decomposed into its elemental motions automatically and the action within the scene may be recognized. This type of capability may enable building a task list or a process map. In a more modern context, other investigators have enabled the determination of actions based on methodologies such as machine learning, convolutional neural networks and recurrent neural networks. See e.g., Yeung et. al, "End-to-end Learning of Action Detection from Frame Glimpses in Video," CVPR, February 2016, http://ai.stanford.edu/~syyeung/frameglimpses.html.

With the concept of the atomic action now described, the hierarchy of a process within a factory may now be explained. Using the same "Retrieve Object" example, a process could be an "assembly of a motherboard", a step could be "manual assembly", a task could be "insert chips", an action could be "retrieve chip" and the atomic actions describing this action could be "search", "find", "select", and "grasp". This explains how a process can be described in its most elemental terms.

In the change recognition capability, changes from an existing reference data is detected. This capability is described in Yeung et. al, "End-to-end Learning of Action Detection from Frame Glimpses in Video", CVPR, February 2016, http://ai.stanfond.edu/~syyeung/frameglimpses.html.

As noted above, computation engine 105 may include process discovery engine 170. Observation station 102 feeds observation data from sensors 104 to computation engine 105. From this observation data, process discovery engine 170 determines a process. As explained earlier, a process comprises or consists of a list of steps. Process discovery engine 170 may automatically generate the list of steps after repeated observation of the actions that occur at the observation site (e.g., workstation). Observations may include observations of objects that are being moved, the locations these objects are moved from and to, the orientation of the objects while they are being transported as well as the interactions between the people and the objects. Even further, observations may include the sequence of steps or the order of steps as well. In one configuration, manager system 100 observes the set of actions at a particular station multiple times. A human operator may review these actions, label each action, and pick a set of actions that best represents the process that is performed at that location. The details of the process are thus generated in this manner. In another configuration, process discovery engine 170 automatically reduces each action to an atomic set of actions. For example, process discovery engine 170 may comprise a deep learning system that is trained to identify an atomic set of actions shown in the observation data. Process discovery engine 170 may describe atomic actions using the Therblig notation. If manager system 100 (e.g., process discovery engine 170 of computation engine 105 of manager system 100) is unable to break down a process into its atomic actions, manager system 100 may send an alert to a human and ask for clarification.

In addition to understanding the process at one location or workstation, if observation stations are set up in all the workstations so that the observation stations can either operate simultaneously or in an individual fashion, then process discovery engine 170 may first discover (i.e., generate knowledge of) the process for each location or each workstation and then may discover the process for all the workstations in each site that conducts activities related to one project.

In some examples, based on the information that computation engine 105 has through observations, computation engine 105 may be able to fill-in missing data. For example, process discovery engine 170 may be able to identify actions that are not shown in observation data. This may be advantageous in various situations, such as when fewer observation stations are deployed than workstations or when occlusions occur so that portions of the scene are not visible. This is explained with an example. In this example, there are 3 steps in a process of producing a long, red product. In a first step, a product is positioned horizontally on a conveyor belt and aligned so that the long axis of the product is parallel to the direction of travel of the belt. This step is observed by an observation system. In a second step, the product is turned 90°. This step is not observed by an observation system. In a third step, the product is painted. The third step is observed. With this information, given no external disturbances, process discovery engine 170 can deduce that the product must have been turned 90° in the second step. This is an example where computation engine 105 fills in the gaps. In some examples, if computation engine 105 determines that one or more actions are not observed, computation engine 105 may automatically request one or more observation stations activate one or more sensors such that the unobserved actions can be included in subsequent observation data. In some examples, computation engine 105 may output an indication to a user to activate such sensors.

In another variation of this example, manager system 100 may have access to a previously developed process for the same or similar activity it is currently observing. If the previously developed process is similar, then manager system 100 may be able to use this as a template to create a new process based on the observed variations. One advantage of this capability is that the time to develop a process based on observations may be shortened. If the previously developed process is the same as the process being observed, then manager system 100 may be able to determine variances from the existing process and alert appropriate personnel or resources.

In another example, once process discovery engine 170 identifies a process, process discovery engine 170 may compare the process to standard practices or to good manufacturing processes. The output of computation engine 105 may indicate whether standard practices or good manufacturing processes are being complied with. For example, computation engine 105 may use a machine learning system trained to identify instances of the process to determine that newly-received observation data represents an instance of the process. In this, example computation engine 105 may compare the additional instance of the process to a standard practice. In this example, computation engine 105 may generate the feedback such that the feedback indicates the additional instance of the process complies with the standard practice.

This type of comparison can provide guidance to further optimize a process or in some cases, may provide metrics on compliance to standards. For example, a process is to cook a hamburger at a restaurant. As is known, it is a regulatory requirement that the cooking process includes a step where the burger has to be exposed to a certain temperature for a minimal period of time so that the native pathogens within the hamburger are destroyed. In this case, the temperature of the cooking process can be monitored and compared against the requirement. If the temperature profile is outside that of the requirement, computation engine 105 can flag an error.

As noted above, computation engine 105 may include causality engine 174. Causality engine 174 may determine, based on observation data and other input, a cause of an issue with a product. When there is an issue with a product, for example when a product is reported to be defective after release or when decreased factory output is observed, typically an effort is made to understand the root cause. In one example, causality engine 174 of manager system 100 can perform or provide data so that root cause analysis can be performed.

For example, the paint on a released product is found to experience deterioration. For the purposes of this example, an assumption is made that this product goes through three work-cells. These work-cells may or may not be in close proximity to each other. In the first work-cell, the part is machined, in the second work-cell, the part is painted and in the third work-cell, the part is packaged. If manager system 100 is installed in all three work-cells and each of observation stations 102 has a visible light camera and an infra-red camera, then the activities and the temperature of the product, and/or an object handling the part, can be monitored and recorded. Objects handling the part may include tools, hands, etc. Through the capability of process discovery engine 170 described above, the timing of when a part is transferred from the first workstation to the second workstation to the third workstation is monitored and noted. Continuing the example, if the temperature of the part was higher than normal in the second workstation but still within the expected range, then causality engine 174 may deduce a possible cause from this knowledge. By providing data to causality engine 174 about the defect and all possible causes of the defect, including the cause that surface temperature during painting may be one cause, a user may command causality engine 174 to examine the observations for the possible causes or causality engine 174 may examine the observations for possible causes automatically. In doing so, in the example above, causality engine 174 may report that the temperature of the part in the second workstation was higher than usual (based on a trend or other historical data). From this knowledge, possible causes can emerge. Possible causes could be that machining process in the first work-cell was raising the temperature of the part higher than normal perhaps because the milling machines were rotating slightly faster than normal and needed tuning. Therefore, in this example, causality engine 174 highlighted two issues: one that the milling machine needed tuning and second that the normal range of temperature was specified incorrectly. With this knowledge, the root cause can be rectified. Thus, causality engine 174 is able to analyze the input information and given an issue and generic information about how the issue may be created, causality engine 174 can search in the database for the possible causes.

There are a number of different ways to implement causality engine 174. In one approach, artificial intelligence and machine learning is used to search for a root cause. FIG. 3A describes this approach. Particularly, FIG. 3A is a block diagram illustrating an example approach that uses artificial intelligence and machine learning to search for a root cause, in accordance with one or more aspects of this disclosure. Here, box 140 depicts a process where there are some inputs and some outputs. In addition to this, a training set 142 may be optionally provided which may comprise or consist of labeled observations. An artificial intelligence (AI) machine is provided the inputs along with the labeled observations of training set 142. The labeled observations can provide characterization data about the process. This characterization data may include but, may is not necessarily limited to, how a human observer rates the process, about successful and unsuccessful runs of the process, etc. Over time, given enough training material, the AI machine can determine whether a process was run appropriately or not and if not, where the failure may have occurred.

Figure 3B:
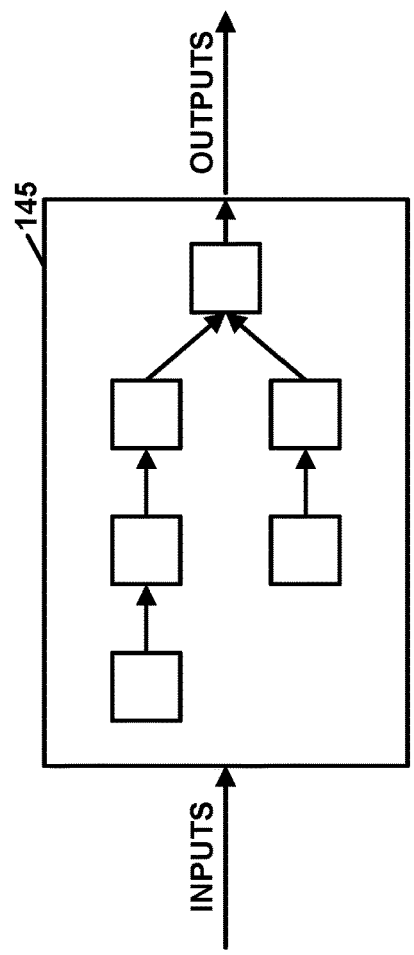
FIG. 3B is a block diagram illustrating an example process in which relevant details about the process are entered into a computational engine, in accordance with one or more aspects of this disclosure.
Figure 3A:
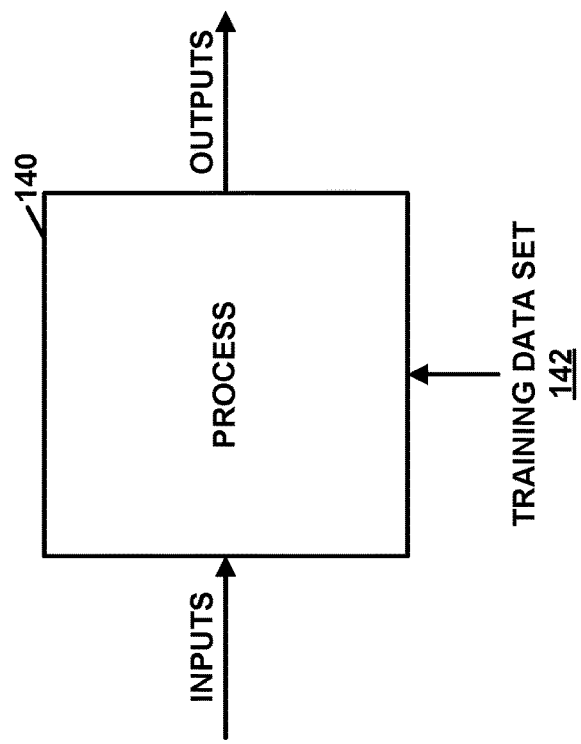
FIG. 3A is a block diagram illustrating an example approach that uses artificial intelligence and machine learning to search for a root cause, in accordance with one or more aspects of this disclosure.

Another approach is described in FIG. 3B. FIG. 3B is a block diagram illustrating an example process in which relevant details about the process are entered into a computational engine, in accordance with one or more aspects of this disclosure. In the example of FIG. 3B, in box 145, which depicts a process, the relevant details about the process (including details about each step, task and action) are entered into the computational engine. The details about the process may be entered into the computational engine by a human operator or process discovery engine 170 may enter the details about the process. In the example of FIG. 3B, the small boxes within box 145 may correspond to steps of the process. During a root cause analysis, causality engine 174 may examine data associated with each step, task and action in order to understand where an error or a variance may have occurred. In one situation, the error or variance may not have occurred at any one work-cell or step or task. Errors may have accumulated along the way resulting in an ultimate failure. In another situation, each step, task or action may have been performed as per specifications but the behavior of the process when the steps, tasks or actions are combined may have led to a failure. While the two approaches described with regard to FIG. 3A and FIG. 3B for implementing causality engine 174 are described above, other approaches are not excluded.

Various types of modeling techniques may be used to implement the sub-engines described above (e.g., process discovery engine 170, analysis engine 172, causality engine 174), alone or in combination. These modeling techniques include, but are not necessarily limited to, statistical and probabilistic modeling techniques. As an example, when a chip is picked, computation engine 105 may calculate the probability that the picked chip is a specific chip from a specific manufacturer. The behavior of manager system 100 can be determined by the magnitude of the probability. For example, if the calculated probability is below 0.5, computation engine 105 may flag errors.

In another example, if during observations of a process, occlusion occurs and certain information regarding a specific chip is not available to computation engine 105, then, based on information that is available, computation engine 105 can calculate the probability of that chip being a specific part from a specific part number.

Figure 4:
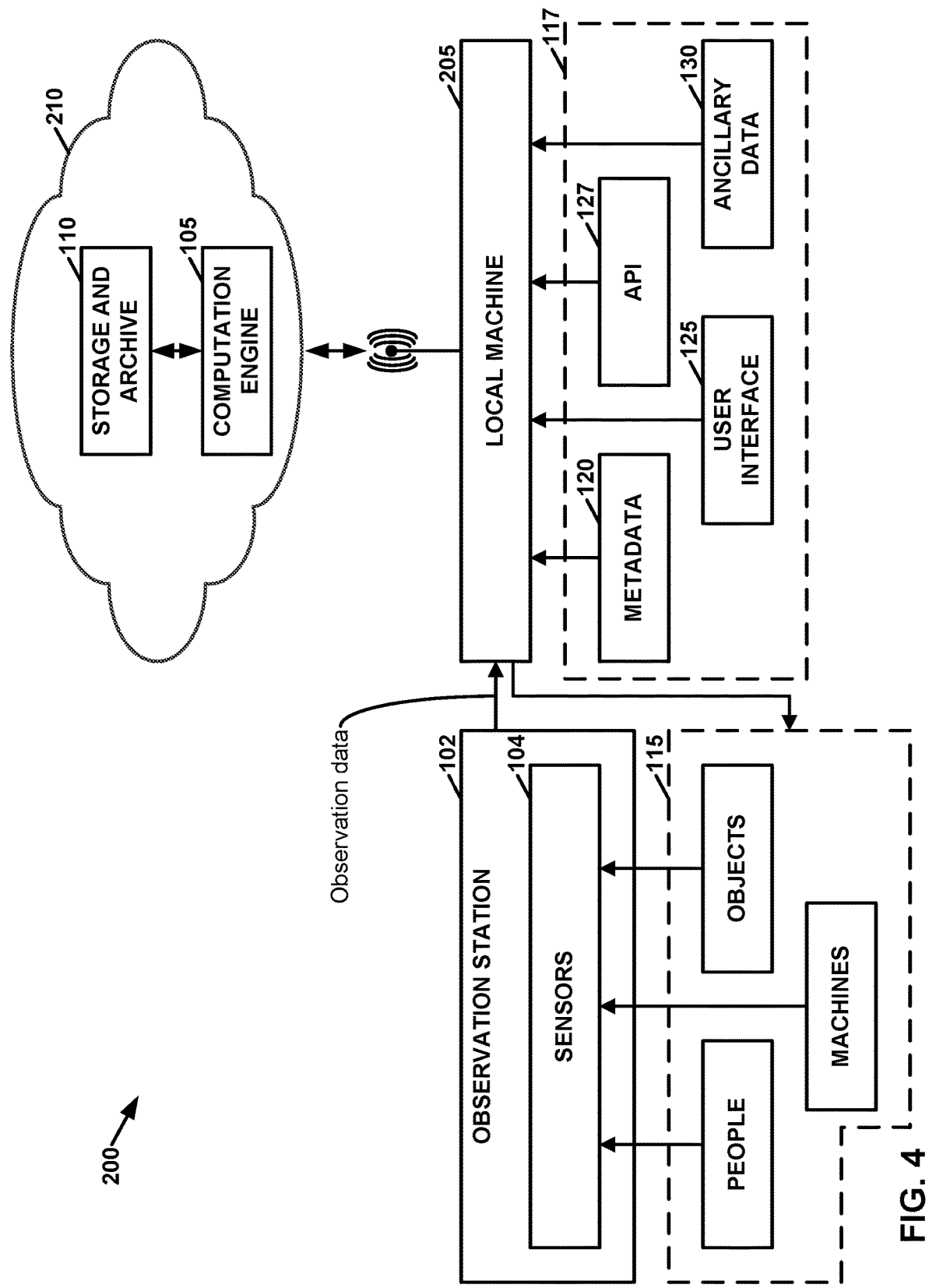
FIG. 4 is a block diagram illustrating an example in which manager system has a distributed architecture, in accordance with one or more aspects of this disclosure.

FIG. 4 is a block diagram illustrating an example in which manager system 100 has a distributed architecture, in accordance with one or more aspects of this disclosure. In contrast to FIG. 1A, where the various components of manager system 100 may have been at one physical location, in FIG. 4, some of the components may be remotely placed in a different physical location. Thus, in the example of FIG. 4, computation engine 105 and storage and archival sub-system 110 are placed remotely as compared to a local machine 205 and observation station 102. Thus, from the perspective of observation station 102 and local machine 205, computation engine 105 and storage and archival sub-system 110 are located in a cloud computing system 210. Local machine 205 functions as a conduit between observation station 102 and a remote computation engine 105 and a storage and archival sub-system 110. Although the example of FIG. 4 shows a wireless connection between local machine 205 and cloud computing system 210, examples of this disclosure may also use wired connections. Implementing computation engine 105 and storage and archival sub-system 110 in a remote capability may have beneficial results. For example, one benefit is that the remote capability may have more computational power than possible in local machine 205. Furthermore, in some examples, more complex analysis may be performed over longer time windows with the larger computational power. Additionally, a remotely-placed storage and archival sub-system 110 may have more capability, such as, but not limited to, increased storage.

Figure 5:
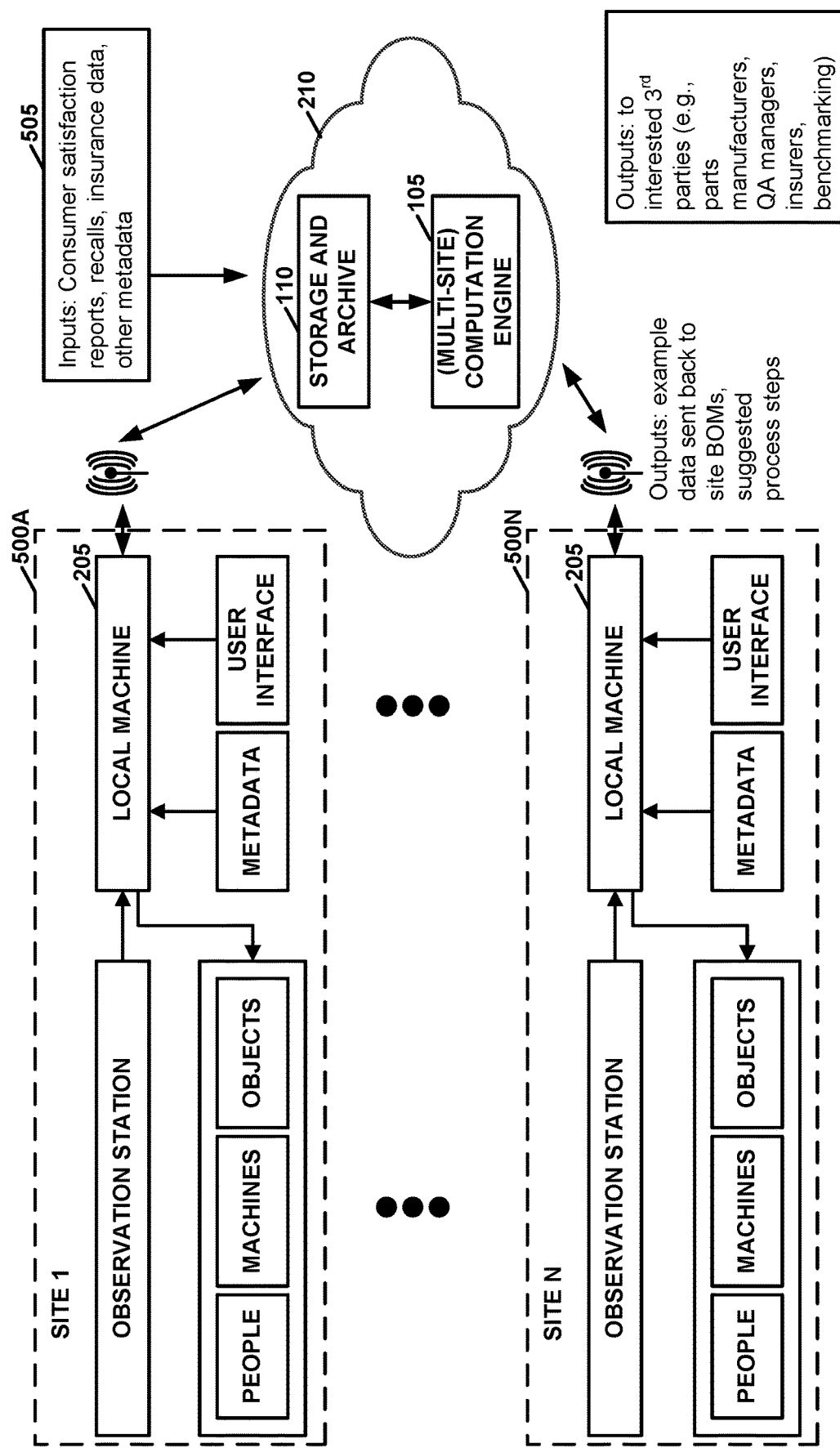
FIG. 5 illustrates another example in which manager system has a distributed architecture, in accordance with one or more aspects of this disclosure.

FIG. 5 illustrates another example in which manager system 100 has a distributed architecture, in accordance with one or more aspects of this disclosure. In the example of FIG. 5, multiple manager systems 500A through 500N (collectively, "manager systems 500") of the type described in FIG. 4 are installed. These stations may be installed at different physical sites (labeled "SITE 1" through "SITE N" in FIG. 5) or multiple stations may be installed at one site or a combination of the two may be installed. Each of these manager systems is connected via to cloud computing system 210. Like in the example of FIG. 5, cloud computing system 210 includes capabilities of computation engine 105 and storage and archival sub-system 110. Computation engine 105 in FIG. 5 and storage and archival sub-system 110 in FIG. 5 are similar to those described earlier, except that computation engine 105 and storage and archival sub-system 110 of FIG. 5 may be configured to assimilate data from multiple sites or stations or both and perform computations on this data set coming from disparate locations. In some examples, computation engine 105 may send various types of outputs back to sites 1 through N. For example, computation engine 105 may send back to sites 1 through N information such as a bill of materials (BOM), suggested process steps, and so on. A BOM may comprise a list of the raw materials, sub-assemblies, intermediate assemblies, sub-components, parts and the quantities of each needed to manufacture an end product. As shown in the example of FIG. 5, other outputs of computation engine 105 may include outputs to interested third parties, such as parts manufacturers, quality assurance (QA) managers, insurers, benchmarking parties, and so on.

As noted above, computation engine 105 may comprise a privacy unit 178 (FIG. 2). In some examples, privacy unit 178 may store privacy settings and implement privacy policies based at least in part on the privacy settings. In one example, privacy settings can be determined and set by plant managers such that the extent of how widely the data of a specific work-cell, line or plant or other groupings of manufacturing stations, becomes available. For example, a plant manager (or someone with authority) can determine that no data about a specific work-cell is to be made available to anyone. In this example, this specific workstation can benefit from the analysis carried out on other data that has some bearing on the work being performed at this cell but the data from this local cell does not contribute to the collective information content. In another example, the plant manager may decide that the data from a specific workstation (or other grouping) can be made available freely. This data can contribute to the collective information content. Various options on the continuum including these two examples are possible and not excluded.

In one example, the privacy settings may be tied to levels of service or cost of service. For example, a management company that manages manager systems (e.g., manager system 100, manager systems 500 (FIG. 5) and is responsible for the data analysis, may charge less in return for having access to the data. Conversely, in this example, the management company may charge more if data is kept private. Various other charging schemes are possible and not excluded.

Privacy models can be implemented in various ways. As described above, explicit policies defining how a specific unit of information (data, results, observations, analysis or other constructs) is treated, shared or is made available to different users or other sub-engines, can be defined by authority figures like the plant manager. In an alternate model, using probability models and past user behavior, privacy unit 178 can determine how a unit of information is treated. These two models can co-exist, with the probabilistic model filling in policies for units of information for which the explicit policies are deemed incomplete or inadequate or incorrect. For this to be possible, the system may continually monitor the products of the units of information. In some examples, a privacy model may be implemented by selectively activating sensors of an observation station. That is, not all sensors including in an observation station are activated to preserve privacy. For example, an observation station at a workstation may include an infrared camera, but the infrared camera may be turned off to protect a worker's privacy.

As indicated in the figures, manager system 100 has multiple inputs. Referring to FIG. 1A, one input is the observation data about people, machines, and objects, gathered through observations by observation station 102. Other inputs include metadata 120, which may comprise metadata related to objects. For example, metadata 120 may include metadata about a specific chip that is being operated on. Yet another input is ancillary data 130, which may relate to other ancillary data such as, but not limited to, inventory management data, line speed personnel files, labor cost by specific regions etc., often available from the business systems used. Input data may also be provided by an operator of the system through user interface 125. These inputs can be used in a variety of ways.

One example is now presented. In this example, data about the reach (of the hand) of the various operators is observed, stored and available. One operator is taller and has a reach of 3.5 feet and a second operator is shorter and has a reach of 3 feet. A robot placing parts on a conveyor belt may decide where to place the part on the belt, depending on the operator. If the shorter operator with the smaller reach is at the work-cell, than the robot may place the part closer to the chair that the operator sits on. Conversely, if the taller operator with the longer reach is at the work-cell, the robot can place the part away from the chair. Thus, this is an example of dynamic optimization based on some inputs, simultaneously improving efficiency and ergonomics.

In box 505 in FIG. 5, some additional types of inputs are illustrated. Particularly, in the example of FIG. 5, additional types of inputs may include consumer satisfaction reports, recalls, insurance data, and other metadata. Inputs from API 127 and ancillary data 130 shown in FIGS. 1A and 1B are not shown in FIG. 5 for the purposes of clarity. This is meant to be an illustrative set and not an exhaustive or a complete list. This list includes but is not limited to consumer satisfaction reports, recalls, insurance data, other metadata. The cloud computing system 210 associates each of these reports with a specific product or components of a product. For each product, the knowledge about where the product was made, how the product was made and when the product was made, may also exist within cloud computing system 210, assuming that observations stations were installed to monitor that product at relevant locations or if the necessary information can be extracted from observations stations even if they were not directly monitoring the relevant locations.

In one example, information about the quality of a part or a product is computed and made available. For instance, in this example, a gear tooth wheel is inserted in a door lock mechanism in one site (site A). However, in another site (site B), the same gear tooth wheel is being inserted in a drill. Assuming that a certain but different percent of the gear teeth fail in both products either during assembly or after product release, manager systems 500 of FIG. 5 may provide the benefit of assimilating data from both products and producing a more comprehensive quality profile for the gear tooth. Some of the aspects that make this type of analysis possible are the ability to observe a manufacturing process and recognize the components that are being used and store this data, the ability to observe, recognize and store data about the failures (such as failure of gear teeth during the manufacturing process), the ability to accept data about the products especially data about failures in the field, the ability to also recall a list of components by just knowing the part, perhaps by recalling a bill-of-material (BOM). With this and other data, cloud computing system 210 calculates a comprehensive quality profile of a part.

In another example, cloud computing system 210 builds a quality profile for multiple parts as described above and builds a library with this information. The library may be queried in various ways including but not limited to by part description, by manufacturer or by part number. Over time, as more information is added to the library, it can provide a benefit to the product designers during the design and sourcing process when the quality and reliability of the product is being estimated or evaluated.

In another example, the quality data or other data about a part or a product can be provided to insurance providers who provide insurance against defective products or products that deteriorate over time.

Figure 6:
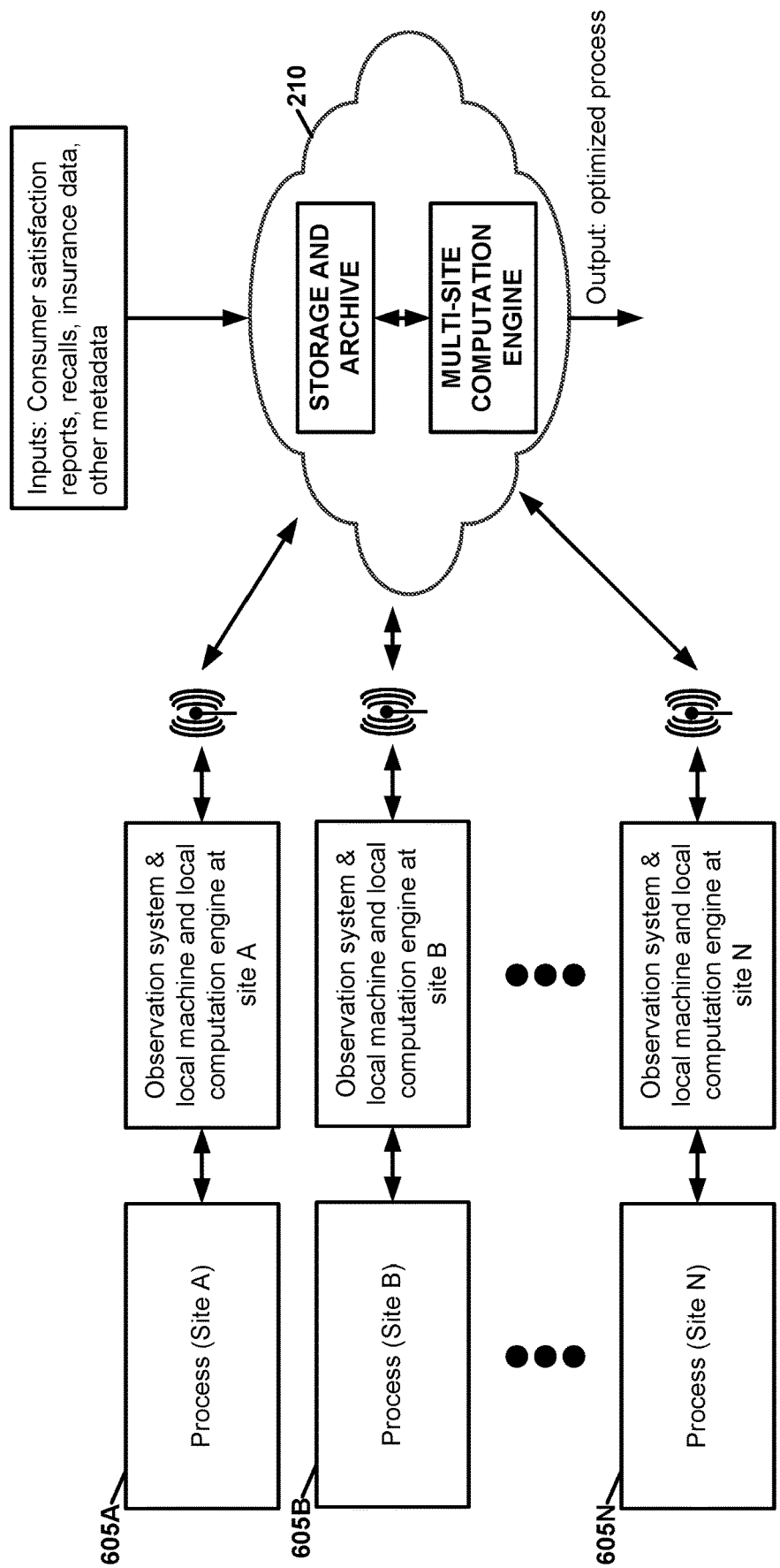
FIG. 6 is a block diagram illustrating an example for automatically identifying a process, in accordance with one or more aspects of this disclosure.

FIG. 6 is a block diagram illustrating an example for automatically identifying a process, in accordance with one or more aspects of this disclosure. In the example of FIG. 6, manager system 100 observes a process for building a specific product or type of product across multiple sites and suggest an optimized process by analyzing the data. In the example of FIG. 6, boxes 605A, 605B, 605N depict that a process for building the same type of product or the same product that is being observed across multiple sites. As before, the sites may be at the same physical location in the vicinity of each other or may be remotely located. These processes are observed and analyzed and an optimized process as defined by a certain set of criteria can be produced as an output. For instance, in this example, the common manufacturing process being observed at the various sites is the soldering of a 2K ohm resistor. No assumption is being made here about the final product. The final products may be same across the various sites or may be different however the common process of soldering is being observed. Also in this example, through observations, it is revealed that the solder temperature and the tip dwell time on the part vary across all sites. In this case, by making these observations across different sites and by determining an optimal tip temperature and dwell time, a recommendation can be made of what these two parameters should be. The optimal settings may be determined by the recommendations from the solder lead manufacturer or by observing the failures of these parts due to inappropriate soldering or by human input or some other method. These recommendations then can be fed back to the sites to the plant managers. A benefit of these recommendations may be to reduce failure of this part and therefore contribute to overall product quality. Thus, this is an example where observations of the same process utilized in the production of different products, possibly produced by different manufacturers, and subsequent analysis led to an optimization of a specific process.

Figure 7:
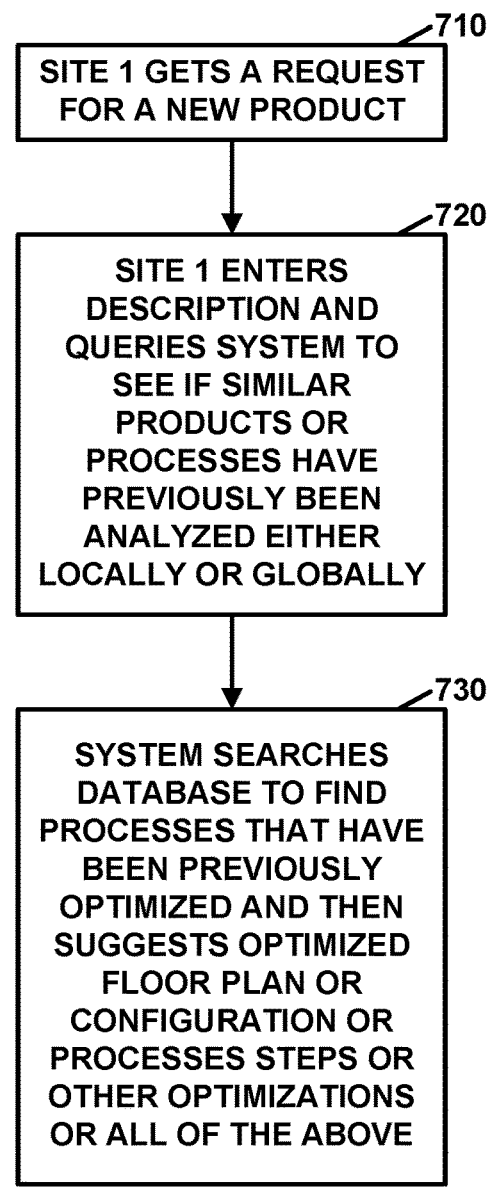
FIG. 7 is a flowchart illustrating an example operation of a system in which a knowledge base is used by a manager system to provide recommendations for how to manufacture a product, in accordance with one or more aspects of this disclosure.

FIG. 7 is a flowchart illustrating an example operation of a system in which a knowledge base is used by a manager system to provide recommendations for how to manufacture a product, in accordance with one or more aspects of this disclosure. The knowledge base built by manager system 100 can be used to provide recommendations for how to manufacture a product. This is illustrated in FIG. 7. In box 710, a site (e.g., Site 1) gets a request to produce a product the site has not produced before. In box 720, plant managers of the site can enter a description of the product and query a database of manager system 100 to see if a similar or same product has been produced elsewhere. If that information exists, then in box 730, manager system 100 can provide details about how the product was produced along with any known issues with that product such as quality issues. It can also provide details about the bill-of-materials, the process, plant configuration and other details.

In yet another example, another output of computation engine 105 can be a recommendation for a redesign of a part. For instance, in this example, a metal collar of a specific length is being installed onto a shaft by a robotic gripper and a high rate of failure to complete this step is occurring. In this example, analysis engine 172 analyzes the situation and generates a report. Continuing with the example, in this report it is evident that if the robot gripper travels 1 mm further down, a 100% success occurs but otherwise there is a 50% chance of success. Having this data, the plant manager has two choices; either the robot can be programmed to travel 1 mm further down or the collar can be redesigned to be 1 mm taller. Providing that the 1 mm longer collar would still be appropriate for the product being produced, the plant manager may well choose that as the solution as reprogramming the robot to move 1 mm down may not be possible due to design constraints. The 1 mm variation in the position of the robot may be occurring due to mechanical slack. Thus, this is an example where the observations lead to a redesign of the part.

In yet another example, one or multiple operators are observed at a work-cell for a specific process occurring at that work-cell. Based on this data, when queried, manager system 100 may output a set of specifications for a robot if the plant managers wanted to adopt automation at this work-cell. Manager system 100 may already know the capabilities of various commercially available robots and can go further and recommend a specific robot by a specific robot manufacturer possibly from a catalog of approved robots. For the purpose of this document, cobots and all forms of automation are referred to as robots.

In another example, if an entire manufacturing line or portions of the manufacturing line are observed, then manager system 100 may be able to provide recommendations of how to change the configuration of the line to optimize the production of parts. The recommendations may include but may not be limited to the placement of specific resources at specific work-cells or changing line speed (making it faster or slower) etc.

In another example, if the manufacturer triggers a recall, manager system 100 can, based on its observations, identify the minimal set of products to be recalled. This capability can be implemented using multiple techniques. In one technique, manager system 100 uses the notion of traceability where manager system 100 can search for all instances where certain observation parameters (e.g., temperature, dwell time, position, length of insertion motion) that caused the recalls are noticed. Thus, using traceability, often across several process steps, only a sub-set of all products produced in a time window can be identified. This type of capability may shorten the duration over which the response to the recalled product is implemented. Many benefits may ensue from such a rapid response capability including ensuring product safety, reduced cost to the company making the product. The concept of traceability can be applied widely across many industries including but not limited to the pharmaceutical, food and agricultural industries.

In another example, information can be gathered, analyzed and used in an intelligent and adaptive manner. For example, intelligence embedded in observation station 102 can, based on the information flowing through, determine when to dynamically increase the rate at which information is being gathered and when to decrease the information. Thus, when operators are taking a break in their workday and parts are not flowing through the system, observation station 102 can "observe" less frequently. Conversely, when observation station 102 notices the beginning of an error condition, observation station 102 can observe more frequently. The same concept may be utilized within computation engine 105. Here the computations can vary in frequency dependent on the observation data.

In another example, benchmarking data for various aspects of manufacturing is created based on observations and is made available globally. These aspects may include but may not be limited to quality of a part or product, efficiency of a line, operator output, etc. For instance, in this example, a plant manager of a company producing memory chips wants to know how his plant compares to other memory chip manufacturing companies. Assuming that the systems described above have been placed at multiple such memory chip manufacturing companies, manager system 100 can produce detailed comparison data. The comparison data may include, but may not be limited to, efficiency, cost to manufacture, number of chips manufactured/hour, resources etc. Benchmarking data may also include ranking data (i.e. the system can provide a rank in one or more categories so that the plant manager can assess how his or her plant/company compares to others in the same field). Various types of inputs can be used to provide this benchmarking data; inputs may include but may not be limited observational data from the various companies, metadata about each company (labor costs, geography, utility costs etc.).

In another example, benchmarking surveys can be conducted based on in-factory conditions. Currently, companies that provide benchmarking data rely on post factory surveys; the questions in these surveys are agnostic to the conditions and the environment of the factory that produces the products related to the survey. The observations and analysis of data collected in a factory can inform the survey questions so that they become more targeted and may be used in a feedback loop to further improve the processes within the factory.

Another example is now described. In a typical factory today, the operations of the factory are supported by a centralized infrastructure. Some elements of this infrastructure include but are not limited to quality control, program management and document control. The system described in this disclosure allows the decentralization of one or many of these functions. As an example, an operator at an assembly line may be able to understand the impact of his or her work within the context of the larger operations occurring at that factory. This type of feedback to an operator can be provided in multiple ways including but not limited to on display screens, on personal phones and printed material. To continue with this example, as a result of the capabilities of the system described in this disclosure, it may be possible for an operator (Operator A) to realize that a part he or she is assembling has twice the failure rate compared to the failure rate of the same part assembled by another operator (Operator B). This realization can empower Operator A to seek out Operator B and modify his or her process so that the failure rate can be reduced. Thus, this is an example where the quality control is decentralized and can be affected at local level rather than at the centralized level.

Figure 8:
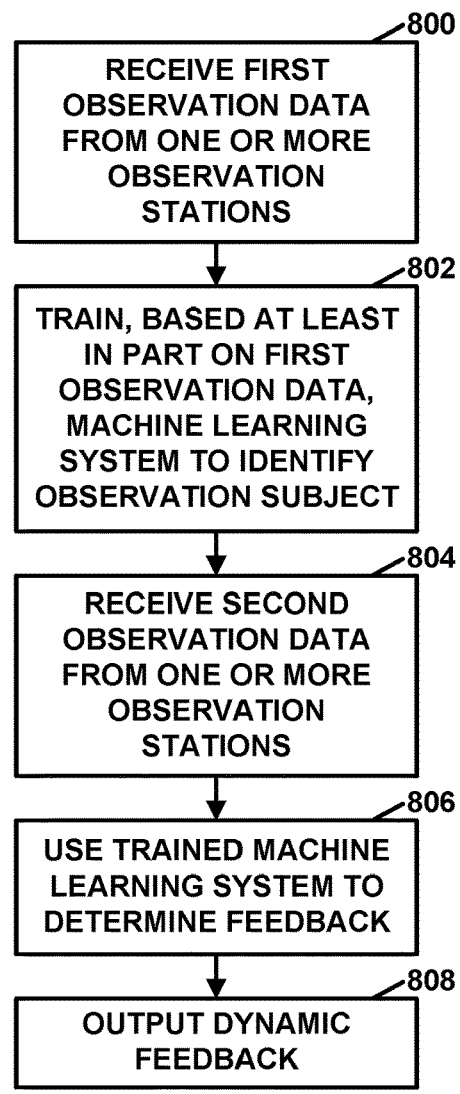
FIG. 8 is a flowchart illustrating an example operation of a manager system, in accordance with one or more aspects of this disclosure.

FIG. 8 is a flowchart illustrating an example operation of manager system 100, in accordance with one or more aspects of this disclosure. In the example of FIG. 8, the one or more physical machines that implement computation engine 105 may receive first observation data from the one or more observation stations (e.g., observation station 102 (FIG. 1A, FIG. 4), observation station/computation engine 102' (FIG. 1B), observation stations at sites 1 through N (FIG. 5), and so on) (800). For instance, computation engine 105 may receive the first observation data from a plurality of observation stations. In this example, the first observation data comprises sensor data collected from observing instances of an observation subject. The observation subject may be various activities or things. For instance, the observation subject may be one or more of a process performed at one or more factories, a step of the process, a task of the step of the process, an action of the task, and a part used or made as part of the process.

Furthermore, in the example of FIG. 8, computation engine 105 may train, based at least in part on the first observation data, a machine learning system (e.g., machine learning system 107) (802). Thus, the first observation data may serve as a training data set for the machine learning system. As described elsewhere in this disclosure, computation engine 105 may train the machine learning system based on other inputs in addition to observation data. For instance, in the example of FIG. 5, the inputs may include consumer satisfaction reports, recalls, insurance data, and other metadata. In some examples, training the machine learning system comprises determining values in vector, such as the space-time vector discussed elsewhere in this disclosure. In some examples, computation engine 105 trains the machine learning system to identify the observation subject.

In some examples where the observation subject is a process, the steps of the process are not known before training begins. Rather, training the machine learning system may comprise computation engine 105 may use the first observation data (i.e., the training data set) to discover the process. For instance, computation engine 105 may use unsupervised learning techniques to analyze the training data set to discover the process. In some examples, as part of training the machine learning system to identify the process, computation engine 105 may determine, based at least in part on the first observation data, a missing step of the process that is not observed by any observation station of the one or more observation stations.

Additionally, in the example of FIG. 8, computation engine 105 may receive, after the machine learning system has been trained, second observation data from the one or more observation stations (804). The second observation data may comprise sensor data collected from observing an additional instance of the observation subject. For example, the first observation data may comprise sensor data collected by observing an action being performed hundreds of times. In this example, the second observation data may comprise sensor data collected while observing the action being performed an additional time.

Furthermore, computation engine 105 may use the trained machine learning system to determine feedback based at least in part on the second observation data (806). Thus, the second observation data may serve as an execution data set for the machine learning system. In various examples, the feedback may take various forms. For example, the feedback may comprise an indication of how to improve the additional instance of the observation subject. For instance, the feedback may comprise an indication of how to improve a duration of a task, an indication of how to improve an assignment of tasks performed as part of a process, an indication of how to improve an order in which the tasks are performed, an indication of how to improve a location at which the tasks are being performed, an indication of parameters that caused a recall of products made at the one or more factories to occur, an indication advising a first operator to seek advice from a second operator based at least in part on the second operator performing the task better than the first operator where the first operator and the second operator both perform the same task, an indication of a recommended robot to perform or assist the action, or another type of feedback.

In the above examples, computation engine 105 may determine the feedback regarding how to improve the duration of the task by first identifying, based on the training data set, a way of performing the task in a least amount of time, determining that a worker is not currently performing the task this way, and providing feedback to the worker regarding how to perform the task in the way identified based on the training data set.

In the above examples, computation engine 105 may determine the feedback regarding how to improve an assignment of tasks by identifying, based on the training data set, one or more workers who perform the task fastest, and generating feedback indicating that the identified workers should perform the task instead of workers who perform the task slower. Computation engine 105 may provide feedback comprising an indication of how to improve an order in which the tasks are performed by identifying, based on training data in which the tasks are performed in various orders, an order of the tasks that yields the best results. In this example, computation engine 105 may receive additional observation data, determine whether the order of tasks represented in the additional observation data matches the identified order, and output feedback indicating how to conform the order represented in the additional observation data to the identifier order.

Computation engine 105 may provide feedback comprising an indication of how to improve a location at which the tasks are performed by identifying, based on training data in which the tasks are performed at various locations, a location for performing the tasks that yields the best results. In this example, computation engine 105 may receive additional observation data, determine whether the location at which tasks represented in the additional observation data corresponds to the identified location, and output feedback indicating how to conform the order represented in the additional observation data to the identifier order.

In one example, computation engine 105 may provide feedback comprising an indication of parameters that caused a recall of products by identifying, based on the training data set, a reference process in which the products do not have the defect that caused the recall. In this example, computation engine 105 may receive additional observation data representing an additional instance of the process which produced a recalled product. Computation engine 105 may then compare the additional instance of the process to the reference process to identify differences that may have resulted in the defect.

In another example, computation engine 105 may determine, based on training data, that a second operator typically performs a task at a particular metric. In this example, computation engine 105 may receive additional data representing a first operator performing the task at a lower metric. Hence, in this example, computation engine 105 may provide feedback comprising an indication advising the first operator to seek advice from the second operator based at least in part on the second operator performing the task better than the first operator.

In another example, computation engine 105 may determine, based on training data set, that an action is being performed at a workstation. In this example, computation engine 105 may determine, based on a catalog of robots, that a particular robot is able to perform the action. Accordingly, in this example, computation engine 105 may generate feedback that comprise an indication of the determined robot.

In another example, the feedback may comprise an indication that the additional instance of the observation subject differs from a reference model. In one example, the reference model is a reference scene, as described elsewhere in this disclosure. In this example, as part of using the trained machine learning system to determine the feedback, computation engine 105 may use the trained machine learning system to determine that the second observation data represents the additional instance of the observation subject. In other words, computation engine 105 uses the trained machine learning system to classify the second observation data into a category of representing the observation subject. Additionally, in this example, computation engine 105 may determine whether the additional instance of the observation subject is different from the reference scene. Computation engine 105 may determine the feedback based at least in part on the scene being different from the reference scene. For instance, supposing that the observation subject is a task of soldering a chip to a circuit board and the second observation data comprises video data, computation engine 105 uses the trained machine learning system to determine that the video data shows a scene of a worker soldering the chip to the circuit board. Additionally, having determined that the video data shows the scene of the worker soldering the chip to the circuit board, computation engine 105 may compare the scene shown in the video data to a reference scene of the chip being soldered to the circuit board. If there are differences between the scene shown in the video data and the reference scene (e.g., in terms of differences in duration to complete the soldering being over or under thresholds, differences in orders of actions, differences in tools used, etc.), computation engine 105 may output indications of these differences as feedback.

In another example, the observation subject is a process performed at one or more factories. In this example, as part of using the trained machine learning system to determine the feedback, computation engine 105 may use the trained machine learning system to determine that the second observation data represents an additional instance of the process. Additionally, in this example, computation engine 105 may compare the additional instance of the process to a standard practice. In this instance, the standard practice may be a written description of the process. In this example, computation engine 105 may generate the feedback such that the feedback indicates the additional instance of the process complies or does not comply with the standard practice.

In another example, the observation subject may be a part and the feedback may indicate a cause of a problem or defect. For example, the observation stations may include a particular observation station. In this example, the one or more sensors included in the particular observation station include an infrared camera that detects a temperature of the part or an object handling the part. Furthermore, in this example, computation engine 105 may be configured such that, as part of using the machine learning system to determine the feedback, computation engine 105 may determine, based at least in part on the temperature, a cause of a defect of the part. For instance, computation engine 105 may compare the temperature to a temperature used in standard practice, where the standard practice is determined by training the machine learning system. Furthermore, computation engine 105 may determine whether the temperature differs from the temperature used in standard practice. In this example, when the temperature differs from the temperature used in standard practice, computation engine 105 may output feedback indicating a cause of the defect was the temperature differing from the temperature used in standard practice.

Subsequently, computation engine 105 may output the feedback (808). Computation engine 105 may output the feedback in various ways. For example, observation stations may have screens or monitors that computation engine 105 may use to communicate the feedback to operators at workstations. In another example, computation engine 105 may output the feedback as an email or as another form of message, as a file, or in some other way.

The observation stations used in the example operation of FIG. 8 may be at various locations. For instance, in one example, such as shown in FIG. 5 and FIG. 6, the one or more observation stations may include a first set of one or more observation stations and a second set of one or more observation stations. In this example, the first set of one or more observation stations is in a first factory and the second set of one or more observation stations is in a second factory. In this example, computation engine 105 may receive the first observation data from the first set of one or more observation stations and computation engine 105 may receive the second observation data from the second set of one or more observation stations. Thus, in this example, the observation stations used for collecting data used in training the machine learning system may be different from the observation station used for collected data on which the feedback is based.

In some examples, each of the observation stations of the one or more observation stations may be physically located at a corresponding workstation in a factory in the one or more factories. In such examples, the corresponding workstation may be a location at which one or more tasks are performed in the step of the process performed at the one or more factories. Each of the one or more tasks may comprise one or more actions.

As mentioned above, computation engine 105 may receive first observation data and second observation data. The first observation data and the second observation data may comprise various sensor data regarding various types of observations. For example, the first observation data and the second observation data may comprise data regarding one or more of: an observation of an object being moved, an observation of locations the object is moved from and to, an observation of an orientation of the object while the object is being transformed, or an observation of an interaction between people and the object.

As noted elsewhere in this disclosure, computing engine 105 may receive input in addition to or instead of observation data from observation stations. For example, computation engine 105 may be configured to receive input data. In this example, the input data may comprise one or more of: process charts (e.g., human-defined or automatically-defined process charts), video data, audio data, consumer satisfaction reports, recall data, insurance data, or other types of data. Computation engine 105 may receive the input data as metadata 120, via user interface 125, via API 127, or as ancillary data 130. In some examples, computation engine 105 is configured to train, based at least in part on the first observation data and the input data, the machine learning system. In some examples, computation engine 105 is configured to use the trained machine learning system to determine feedback based at least in part on the second observation data and the input data.

Thus, in one example, computation engine 105 may receive first data. In this example, the first data comprises at least one of: first observation data from one or more observation stations or first input data. The first observation data may comprise sensor data collected from observing instances of an observation subject. The observation subject may be in a group comprising: a process performed at one or more factories, a step of the process, a task of the step of the process, an action of the task, and a part used or made as part of the process. In this example, the first input data may comprise one or more of: a first process chart, first video data, first audio data, a first consumer satisfaction report, first recall data, and first insurance data. In this example, computation engine 105 may train, based at least in part on the first data, a machine learning system. Additionally, in this example, computation engine 105 may receive, after the machine learning system has been trained, second data from the one or more observation stations. The second data may comprise at least one of: second observation data or second input data. The second observation data may comprise sensor data collected from observing an additional instance of the observation subject. The second input data may comprise one or more of: a second process chart, second video data, second audio data, a second consumer satisfaction report, second recall data, and second insurance data. Additionally, in this example, computation engine 105 may use the trained machine learning system to determine feedback based at least in part on the second data. The feedback may comprise at least one of: an indication of how to improve the additional instance of the observation subject and an indication that the additional instance of the observation subject differs from a reference model. Furthermore, in this example, computation engine 105 may output the feedback.

Figure 9:
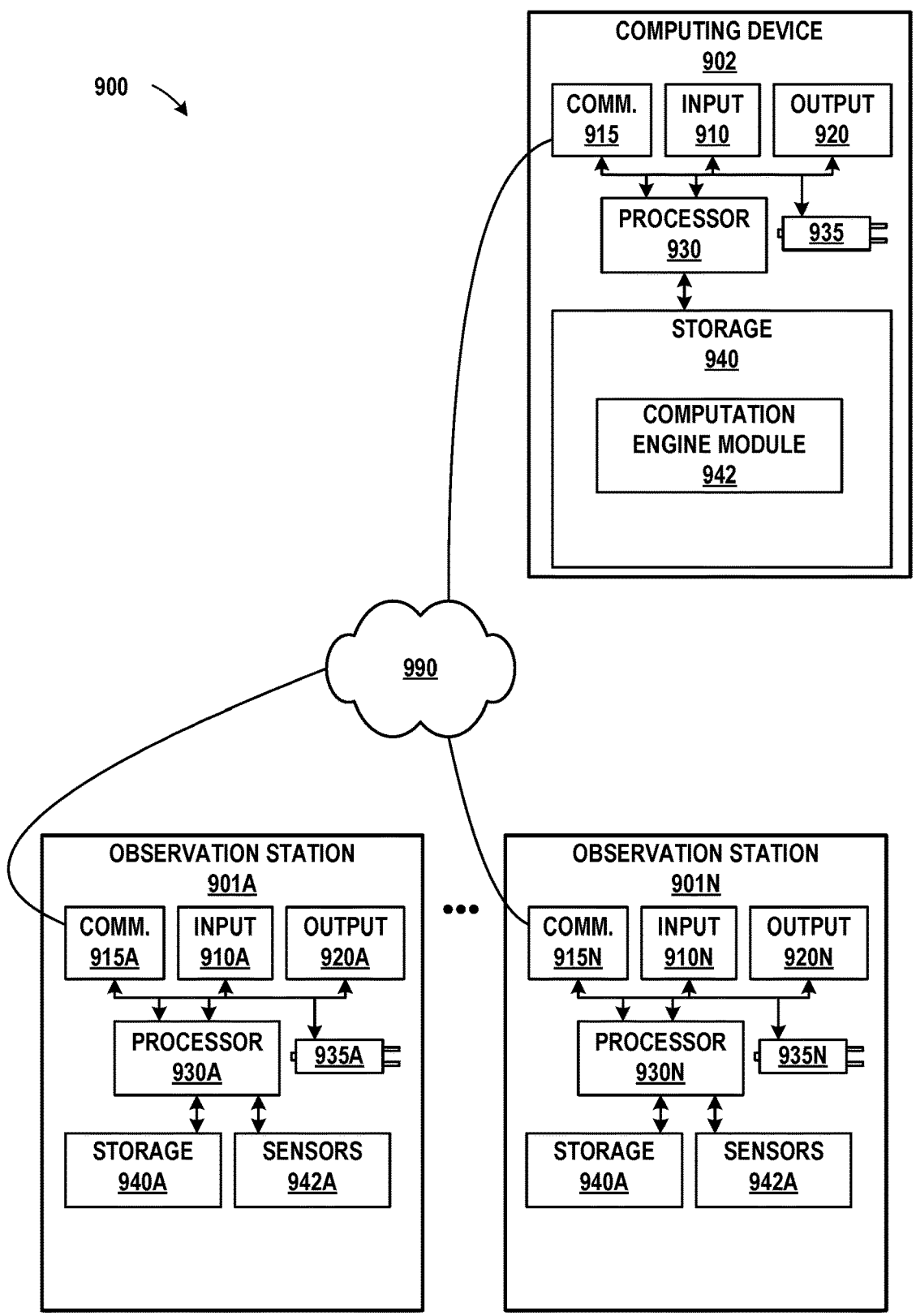
FIG. 9 is a block diagram illustrating an example manager system that is configured in accordance with one or more aspects of the present disclosure.

FIG. 9 is a block diagram illustrating an example manager system 900 that is configured in accordance with one or more aspects of the present disclosure. Manager system 900 of FIG. 9 is described below as an example or alternate implementation of manager system 100 of FIG. 1. However, FIG. 9 illustrates only one particular example or alternate implementation of manager system 100, and many other example or alternate implementations of content distribution system 100 may be used or may be appropriate in other instances. Such implementations may include a subset of the components included in the example of FIG. 9 or may include additional components not shown in the example of FIG. 9. Computing device 902 may communicate with observation stations 901A through 901N (collectively, "observation stations 901") through a network 990.

Computing device 902 of FIG. 9 implements computation engine 105 (FIG. 1). Computing device 902 includes power source 935, one or more input devices 910, one or more communication units 915, one or more output devices 920, one or more processors 930, and one or more storage devices 940. One or more storage devices 940 may include a computation engine module 942. One or more of the devices, modules, storage areas, or other components of computing device 902 may be interconnected to enable inter-component communications (physically, communicatively, and/or operatively). In some examples, such connectivity may be provided by through system bus, a network connection, an inter-process communication data structure, or any other method for communicating data.

Power source 935 may provide power to one or more components of computing device 902. Power source 935 may receive power from the primary alternative current (AC) power supply in a building, home, or other location. In other examples, power source 935 may be a battery. In still further examples, computing device 902 and/or power source 935 may receive power from another source. Power source 935 may have intelligent power management or consumption capabilities, and may such features may be controlled, accessed, or adjusted by one or more modules of computing device 902 and/or by one or more processors 930 to intelligently consume, allocate, supply, or otherwise manage power.

One or more input devices 910 of computing device 902 may generate, receive, or process input. Such input may include input from a keyboard, pointing device, voice responsive system, video camera, button, sensor, mobile device, control pad, microphone, presence-sensitive screen, network, or any other type of device for detecting input from a human or machine.

One or more output devices 920 of computing device 902 may generate, receive, or process output. Examples of output are tactile, audio, visual, and/or video output. Output devices 920 may include a display, sound card, video graphics adapter card, speaker, presence-sensitive screen, one or more USB interfaces, video and/or audio output interfaces, or any other type of device capable of generating tactile, audio, video, or other output. Output devices 920 may include a display device, which may function as an output device using technologies including liquid crystal displays (LCD), dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output.

One or more communication units 915 of computing device 902 may communicate with devices external to computing device 902 by transmitting and/or receiving data, and may operate, in some respects, as both an input device and an output device. In some examples, communication units 915 may communicate with other devices over a network. In other examples, communication units 915 may send and/or receive radio signals on a radio network such as a cellular radio network. In other examples, communication units 915 of computing device 902 may transmit and/or receive satellite signals on a satellite network such as a Global Positioning System (GPS) network. Examples of communication units 915 include a network interface card (e.g. such as an Ethernet card), an optical transceiver, a radio frequency transceiver, a GPS receiver, or any other type of device that can send and/or receive information. Other examples of communication units 915 may include Bluetooth®, GPS, 3G, 4G, and Wi-Fi® radios found in mobile devices as well as Universal Serial Bus (USB) controllers and the like. In accordance with aspects of this disclosure, communication units 915 may receive observation data from observation stations 901A through 901N (collectively, "observation stations 901").

One or more processors 930 of computing device 902 may implement functionality and/or execute instructions associated with computing device 902. Examples of processors 930 include microprocessors, application processors, display controllers, auxiliary processors, one or more sensor hubs, and any other hardware configured to function as a processor, a processing unit, or a processing device. Computing device 902 may use one or more processors 930 to perform operations in accordance with one or more aspects of the present disclosure using software, hardware, firmware, or a mixture of hardware, software, and firmware residing in and/or executing at computing device 902.

One or more storage devices 940 within computing device 902 may store information for processing during operation of computing device 902. In some examples, one or more storage devices 940 are temporary memories, meaning that a primary purpose of the one or more storage devices is not long-term storage. Storage devices 940 on computing device 902 may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art. Storage devices 940, in some examples, also include one or more computer-readable storage media. Storage devices 940 may be configured to store larger amounts of information than volatile memory. Storage devices 940 may further be configured for long-term storage of information as non-volatile memory space and retain information after activate/off cycles. Examples of non-volatile memories include magnetic hard disks, optical discs, floppy disks, Flash memories, or forms of electrically programmable memories (EPROM) or electrically erasable and programmable (EEPROM) memories. Storage devices 940 may store program instructions and/or data associated with one or more of the modules described in accordance with one or more aspects of this disclosure.

One or more processors 930 and one or more storage devices 940 may provide an operating environment or platform for one or one more modules, which may be implemented as software, but may in some examples include any combination of hardware, firmware, and software. One or more processors 930 may execute instructions and one or more storage devices 940 may store instructions and/or data of one or more modules. The combination of processors 930 and storage devices 940 may retrieve, store, and/or execute the instructions and/or data of one or more applications, modules, or software. Processors 930 and/or storage devices 940 may also be operably coupled to one or more other software and/or hardware components, including, but not limited to, one or more of the components illustrated in FIG. 9.

One or more modules illustrated in FIG. 9 as being included within storage devices 940 (or modules otherwise described herein) may perform operations described using software, hardware, firmware, or a mixture of hardware, software, and firmware residing in and/or executing at computing device 902. Computing device 902 may execute each of the module(s) with multiple processors or multiple devices. Computing device 902 may execute one or more of such modules as a virtual machine executing on underlying hardware. One or more of such modules may execute as one or more services of an operating system or computing platform. One or more of such modules may execute as one or more executable programs at an application layer of a computing platform.

Computation engine module 942 may generally perform tasks relating to computation engine 105 as described elsewhere in this disclosure. For example, execution of instructions associated with computation engine module 942 may configure computing device 902 to receive first observation data from one or more observation stations. The first observation data may comprise sensor data collected from observing instances of an observation subject. In some instances, the observation subject may be in a group consisting of: a process performed at one or more factories, a step of the process, a task of the step of the process, an action of the task, and a part used or made as part of the process. Additionally, execution of instructions associated with computation engine module 942 may cause computing device 902 to train, based at least in part on the first observation data, a machine learning system. Furthermore, execution of instructions associated with computation engine module 942 may configure computing device 902 to receive, after the machine learning system has been trained, second observation data from the one or more observation stations. The second observation data may comprise sensor data collected from observing an additional instance of the observation subject. Execution of instructions associated with computation engine module 942 may also cause computing device 902 to use the trained machine learning system to determine feedback based at least in part on the second observation data. The feedback may comprise at least one of: an indication of how to improve the additional instance of the observation subject and an indication that the additional instance of the observation subject differs from a reference model. Additionally, execution of instructions associated with computation engine module 942 may cause computing device 902 to output the feedback.

Computation engine module 942 may interact with and/or operate in conjunction with one or more modules of computing device 902. Computation engine module 942 may receive observation data and other inputs. Computation engine module 942 may receive observation data from communication units 915.

Observation station 901A of FIG. 9 may include power source 935A, one or more input devices 910A, one or more communication units 915A, one or more output devices 920A, one or more processors 930A, one or more storage devices 940A, and one or more sensors 942A. One or more of the devices, modules, storage areas, or other components of observation station 901A may be interconnected to enable inter-component communications (physically, communicatively, and/or operatively). In some examples, such connectivity may be provided by through system bus, a network connection, an inter-process communication data structure, or any other method for communicating data. Correspondingly, observation station 901N may include power source 935N, one or more input devices 910N, one or more communication units 915N, one or more output devices 920N, one or more processors 930N, one or more storage devices 940N, and one or more sensors 942N, which may include the same or similar capability, features, and/or functionality as similarly numbered components of observation station 901A. In some examples, and for certain observation stations 901, one or more components, devices, or modules shown in FIG. 9 as being included within one or more observation stations 901 may be optional.

Certain aspects of observation stations 901 are described below with respect to observation station 901A. Other observation stations 901 may be described similarly, and may also include the same, similar, or corresponding components, devices, modules, functionality, and/or other features. Descriptions herein with respect to observation station 901A may correspondingly apply to one or more other observation stations 901. In some examples, and as may be noted, one or more observation stations 901 may include more or fewer capabilities, features, components, and/or functionality than other observation stations 901.

Power source 935A may provide power to one or more components of observation station 901A. In some examples, power source 935A may be a battery. In other examples, power source 935A may receive power from the primary alternative current (AC) power supply in a building, home, or other location. In still further examples, observation station 901A and/or power source 935A may receive power from another source. Power source 935A may have intelligent power management or consumption capabilities, and may such features may be controlled, accessed, or adjusted by one or more modules of observation station 901A and/or by one or more processors 930A to intelligently consume, allocate, supply, or otherwise manage power.

One or more input devices 910A of observation station 901A may generate, receive, or process input. Such input may include input from a keyboard, pointing device, voice responsive system, video camera, button, sensor, mobile device, control pad, microphone, presence-sensitive screen, network, or any other type of device for detecting input from a human or machine. One or more output devices 920A of observation station 901A may generate, receive, or process output. Examples of output are tactile, audio, visual, and/or video output. Output devices 920A may include a display, sound card, video graphics adapter card, speaker, presence-sensitive screen, one or more USB interfaces, video and/or audio output interfaces, or any other type of device capable of generating tactile, audio, video, or other output. Output devices 920A may include a display device, which may function as an output device using technologies including liquid crystal displays (LCD), dot matrix displays, light emitting diode (LED) displays, organic light-emitting diode (OLED) displays, cathode ray tube (CRT) displays, e-ink, or monochrome, color, or any other type of display capable of generating tactile, audio, and/or visual output. In some examples, observation station 901A may include a presence-sensitive display that may serve as a user interface device that operates both as one or more input devices 910A and one or more output devices 920A.

One or more communication units 915A of observation station 901A may communicate with devices external to observation station 901A by transmitting and/or receiving data, and may operate, in some respects, as both an input device and an output device. In some examples, communication unit 915A may communicate with other devices over a network. In other examples, communication units 915A may send and/or receive radio signals on a radio network such as a cellular radio network. In other examples, communication units 915A of observation station 901A may transmit and/or receive satellite signals on a satellite network such as a Global Positioning System (GPS) network. Examples of communication units 915A include a network interface card (e.g. such as an Ethernet card), an optical transceiver, a radio frequency transceiver, a GPS receiver, or any other type of device that can send and/or receive information. Other examples of communication units 915A may include Bluetooth®, GPS, 3G, 4G, and Wi-Fi® radios found in mobile devices as well as Universal Serial Bus (USB) controllers and the like.

One or more processors 930A of observation station 901A may implement functionality and/or execute instructions associated with observation station 901A. Examples of processors 930A include microprocessors, application processors, display controllers, auxiliary processors, one or more sensor hubs, and any other hardware configured to function as a processor, a processing unit, or a processing device. Observation station 901A may use one or more processors 930A to perform operations in accordance with one or more aspects of the present disclosure using software, hardware, firmware, or a mixture of hardware, software, and firmware residing in and/or executing at observation station 901A.

One or more storage devices 940A within observation station 901A may store information for processing during operation of observation station 901A. In some examples, one or more storage devices 940A are temporary memories, meaning that a primary purpose of the one or more storage devices is not long-term storage. Storage devices 940A on observation station 901A may be configured for short-term storage of information as volatile memory and therefore not retain stored contents if deactivated. Examples of volatile memories include random access memories (RAM), dynamic random access memories (DRAM), static random access memories (SRAM), and other forms of volatile memories known in the art. Storage devices 940A, in some examples, also include one or more computer-readable storage media. Storage devices 940A may be configured to store larger amounts of information than volatile memory. Storage devices 940A may further be configured for long-term storage of information as non-volatile memory space and retain information after activate/off cycles. Examples of non-volatile memories include magnetic hard disks, optical discs, floppy disks, Flash memories, or forms of electrically programmable memories (EPROM) or electrically erasable and programmable (EEPROM) memories. Storage devices 940A may store program instructions and/or data associated with one or more of the modules described in accordance with one or more aspects of this disclosure.

One or more processors 930A and one or more storage devices 940A may provide an operating environment or platform for one or one more modules, which may be implemented as software, but may in some examples include any combination of hardware, firmware, and software. One or more processors 930A may execute instructions and one or more storage devices 940A may store instructions and/or data of one or more modules. The combination of processors 930A and storage devices 940A may retrieve, store, and/or execute the instructions and/or data of one or more applications, modules, or software. Processors 930A and/or storage devices 940A may also be operably coupled to one or more other software and/or hardware components, including, but not limited to, one or more of the components illustrated in FIG. 9.

It is to be recognized that depending on the example, certain acts or events of any of the techniques described herein can be performed in a different sequence, may be added, merged, or left out altogether (e.g., not all described acts or events are necessary for the practice of the techniques). Moreover, in certain examples, acts or events may be performed concurrently, e.g., through multi-threaded processing, interrupt processing, or multiple processors, rather than sequentially.

In one or more examples, the functions described may be implemented in hardware, software, firmware, or any combination thereof. If implemented in software, the functions may be stored on or transmitted over, as one or more instructions or code, a computer-readable medium and executed by a hardware-based processing unit. Computer-readable media may include computer-readable storage media, which corresponds to a tangible medium such as data storage media, or communication media including any medium that facilitates transfer of a computer program from one place to another, e.g., according to a communication protocol. In this manner, computer-readable media generally may correspond to (1) tangible computer-readable storage media which is non-transitory or (2) a communication medium such as a signal or carrier wave. Data storage media may be any available media that can be accessed by one or more computers or one or more processing circuits to retrieve instructions, code and/or data structures for implementation of the techniques described in this disclosure. A computer program product may include a computer-readable medium.

By way of example, and not limitation, such computer-readable storage media can comprise RAM, ROM, EEPROM, CD-ROM or other optical disk storage, magnetic disk storage, or other magnetic storage devices, flash memory, cache memory, or any other medium that can be used to store desired program code in the form of instructions or data structures and that can be accessed by a computer. Also, any connection is properly termed a computer-readable medium. For example, if instructions are transmitted from a website, server, or other remote source using a coaxial cable, fiber optic cable, twisted pair, digital subscriber line (DSL), or wireless technologies such as infrared, radio, and microwave, then the coaxial cable, fiber optic cable, twisted pair, DSL, or wireless technologies such as infrared, radio, and microwave are included in the definition of medium. It should be understood, however, that computer-readable storage media and data storage media do not include connections, carrier waves, signals, or other transient media, but are instead directed to non-transient, tangible storage media. Disk and disc, as used herein, includes compact disc (CD), laser disc, optical disc, digital versatile disc (DVD), floppy disk and Blu-ray disc, where disks usually reproduce data magnetically, while discs reproduce data optically with lasers. Combinations of the above should also be included within the scope of computer-readable media.

Functionality described in this disclosure may be performed by fixed function and/or programmable processing circuitry. For instance, instructions may be executed by fixed function and/or programmable processing circuitry. Such processing circuitry may include one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor," as used herein may refer to any of the foregoing structure or any other structure suitable for implementation of the techniques described herein. In addition, in some aspects, the functionality described herein may be provided within dedicated hardware and/or software modules configured for encoding and decoding, or incorporated in a combined codec. Also, the techniques could be fully implemented in one or more circuits or logic elements. Processing circuits may be coupled to other components in various ways. For example, a processing circuit may be coupled to other components via an internal device interconnect, a wired or wireless network connection, or another communication medium.

The techniques of this disclosure may be implemented in a wide variety of devices or apparatuses, including a wireless handset, an integrated circuit (IC) or a set of ICs (e.g., a chip set). Various components, modules, or units are described in this disclosure to emphasize functional aspects of devices configured to perform the disclosed techniques, but do not necessarily require realization by different hardware units.

Various examples have been described. These and other examples are within the scope of the following claims.

What is claimed is:

1. A system comprising:
   one or more observation stations, each observation station of the one or more observation stations comprising a corresponding set of one or more sensors; and
   one or more physical machines that implement a computation engine configured to:
   receive first observation data from the one or more observation stations, the first observation data comprising sensor data collected from observing instances of an observation subject, the observation subject being in a group consisting of: a process performed at one or more factories, a step of the process, a task of the step of the process, an action of the task, and a part used or made as part of the process;
   train, based at least in part on the first observation data, a machine learning system;
   receive, after the machine learning system has been trained, second observation data from the one or more observation stations, the second observation data comprising sensor data collected from observing an additional instance of the observation subject;

use the trained machine learning system to determine feedback based at least in part on the second observation data, the feedback comprising at least one of: an indication of how to improve the additional instance of the observation subject and an indication that the additional instance of the observation subject differs from a reference model; and output the feedback.

2. The system of claim 1, wherein:

the one or more observation stations include a first set of one or more observation stations and a second set of one or more observation stations, the first set of one or more observation stations is in a first factory, the second set of one or more observation stations is in a second factory, the computation engine receives the first observation data from the first set of one or more observation stations, and the computation engine receives the second observation data from the second set of one or more observation stations.

3. The system of claim 1, wherein each observation station of the one or more observation stations is physically located at a corresponding workstation in a factory in the one or more factories, the corresponding workstation being a location at which one or more tasks are performed in the step of the process performed at the one or more factories, each of the one or more tasks comprising one or more actions.

4. The system of claim 1, wherein the feedback comprises one or more of:

an indication of how to improve a duration of the task, an indication of how to improve an assignment of tasks performed as part of the process, an indication of how to improve an order in which the tasks are performed, an indication of how to improve a location at which the tasks are being performed, an indication of parameters that caused a recall of products made at the one or more factories to occur, an indication advising a first operator to seek advice from a second operator based at least in part on the second operator performing the task better than the first operator, wherein the first operator and the second operator both perform the task, or an indication of a recommended robot to perform or assist the action.

5. The system of claim 1, wherein at least one of the first observation data and the second observation data comprises data regarding one or more of: an observation of an object being moved, an observation of locations the object is moved from and to, an observation of an orientation of the object while the object is being transformed, or an observation of an interaction between people and the object.

6. The system of claim 1, wherein the one or more observation stations includes a plurality of observation stations, and the computation engine is configured to receive the first observation data from the plurality of observation stations.

7. The system of claim 1, wherein the reference model is a reference scene and the computation engine is configured such that, as part of using the trained machine learning system to determine the feedback, the computation engine:

uses the trained machine learning system to determine that the second observation data represents the additional instance of the observation subject;

determines whether the additional instance of the observation subject is different from the reference scene; and determines the feedback based at least in part on the scene being different from the reference scene.

8. The system of claim 1, wherein the observation subject is the process performed at the one or more factories and the computation engine is configured such that, as part of using the trained machine learning system to determine the feedback, the computation engine:

uses the trained machine learning system to determine that the second observation data represents an additional instance of the process;

compares the additional instance of the process to a standard practice; and generates the feedback such that the feedback indicates the additional instance of the process complies with the standard practice.

9. The system of claim 1, wherein the observation subject is the process being performed at the one or more factories, the computation engine is configured such that, as part of training the machine learning system, the computation engine determines, based at least in part on the first observation data, a missing step of the process that is not observed by any observation station of the one or more observation stations.

10. The system of claim 1, wherein:

the one or more observation stations include a particular observation station, wherein the one or more sensors included in the particular observation station include an infrared camera that detects a temperature of the part or an object handling the part; and the computation engine is configured such that, as part of using the trained machine learning system to determine the feedback, the computation engine determines, based at least in part on the temperature, a cause of a defect of the part.

11. The system of claim 1, wherein:

the computation engine is further configured to receive input data, the input data comprising one or more of: process charts, video data, audio data, consumer satisfaction reports, recall data, and insurance data;

at least one of:

the computation engine is configured to train, based at least in part on the first observation data and the input data, the machine learning system; or the computation engine is configured to use the trained machine learning system to determine feedback based at least in part on the second observation data and the input data.

12. A method comprising:

receiving, by one or more physical machines that implement a computation engine, first observation data comprising sensor data collected from observing instances of an observation subject, the observation subject being in a group consisting of: a process performed at one or more factories, a step of the process, a task of the step of the process, an action of the task, and a part used or made as part of the process;

training, by the computation engine, based at least in part on the first observation data, a machine learning system;

receiving, by the computation engine, after the machine learning system has been trained, second observation data from the one or more observation stations, the second observation data comprising sensor data collected from observing an additional instance of the observation subject;

using, by the computation engine, the trained machine learning system to determine feedback based at least in part on the second observation data, the feedback comprising at least one of: an indication of how to improve the additional instance of the observation subject and an indication that the additional instance of the observation subject differs from a reference model; and outputting, by the computation engine, the feedback.

13. The method of claim 12, wherein:

the one or more observation stations include a first set of one or more observation stations and a second set of one or more observation stations, the first set of one or more observation stations is in a first factory, the second set of one or more observation stations is in a second factory, the computation engine receives the first observation data from the first set of one or more observation stations, and the computation engine receives the second observation data from the second set of one or more observation stations.

14. The method of claim 12, wherein each observation station of the one or more observation stations is physically located at a corresponding workstation in a factory in the one or more factories, the corresponding workstation being a location at which one or more tasks are performed in the step of the process performed at the one or more factories, each of the one or more tasks comprising one or more actions.

15. The method of claim 12, wherein using the trained machine learning system to determine the feedback comprises using the trained machine learning system to determine feedback comprising one or more of:

an indication of how to improve a duration of the task, an indication of how to improve an assignment of tasks performed as part of the process, an indication of how to improve an order in which the tasks are performed, an indication of how to improve a location at which the tasks are being performed, an indication of parameters that caused a recall of products made at the one or more factories to occur, an indication advising a first operator to seek advice from a second operator based at least in part on the second operator performing the task better than the first operator, wherein the first operator and the second operator both perform the task in the factory, or an indication of a recommended robot to perform or assist the action.

16. The method of claim 12, wherein the reference model is a reference scene and determining the feedback comprises:

using, by the computation engine, the trained machine learning system to determine that the second observation data represents the additional instance of the observation subject;

determining, by the computation engine, whether the additional instance of the observation subject is different from the reference scene; and determining, by the computation engine, the feedback based at least in part on the scene being different from the reference scene.

17. The method of claim 12, wherein the observation subject is the process performed at the one or more factories and the using the trained machine learning system to determine the feedback comprises:

using, by the computation engine, the trained machine learning system to determine that the second observation data represents an additional instance of the process;

comparing, by the computation engine, the additional instance of the process to a standard practice; and generating, by the computation engine, the feedback such that the feedback indicates the additional instance of the process complies with the standard practice.

18. The method of claim 12, wherein the observation subject is the process being performed at the one or more factories, and training the machine learning system comprises determining, by the computation engine, based at least in part on the first observation data, a missing step of the process that is not observed by any observation station of the one or more observation stations.

19. The method of claim 12, wherein:

the one or more observation stations include a particular observation station, wherein the one or more sensors included in the particular observation station include an infrared camera that detects a temperature of the part or an object handling the part; and using the trained machine learning system to determine the feedback comprises determining, by the computation engine, based at least in part on the temperature, a cause of a defect of the part.

20. A computing system comprising one or more physical machines that implement a computation engine configured to:

receive first data, the first data comprising at least one of: first observation data from one or more observation stations or first input data, the first observation data comprising sensor data collected from observing instances of an observation subject, the observation subject being in a group consisting of: a process performed at one or more factories, a step of the process, a task of the step of the process, an action of the task, and a part used or made as part of the process, the first input data comprising one or more of: a first process chart, first video data, first audio data, a first consumer satisfaction report, first recall data, and first insurance data;

train, based at least in part on the first data, a machine learning system;

receive, after the machine learning system has been trained, second data from the one or more observation stations, the second data comprising at least one of: second observation data or second input data, the second observation data comprising sensor data collected from observing an additional instance of the observation subject, the second input data comprising one or more of: second a second process chart, second video data, second audio data, a second consumer satisfaction report, second recall data, and second insurance data;

use the trained machine learning system to determine feedback based at least in part on the second data, the feedback comprising at least one of: an indication of how to improve the additional instance of the observation subject and an indication that the additional instance of the observation subject differs from a reference model; and output the feedback.

* * * * *